US012673978B2

(12) United States Patent
Epple et al.

(10) Patent No.: US 12,673,978 B2
(45) Date of Patent: Jul. 7, 2026

(54) INCREASING RESISTANCE AGAINST FUNGAL INFECTIONS IN PLANTS

(71) Applicants: BASF SE, Ludwigshafen (DE); Chris Epple; Dennis Epple; Kevin Epple

(72) Inventors: Petra Epple; Brody John DeYoung, Research Triangle Park, NC (US); Holger Schultheiss, Limburgerhof (DE); Ralf Flachmann, Limburgerhof (DE); David A. Hubert, Durham, NC (US); Anne-Christina Herwig, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/780,188

(22) PCT Filed: Nov. 25, 2020

(86) PCT No.: PCT/EP2020/083329
§ 371 (c)(1),
(2) Date: May 26, 2022

(87) PCT Pub. No.: WO2021/105191
PCT Pub. Date: Jun. 3, 2021

(65) Prior Publication Data
US 2023/0002455 A1      Jan. 5, 2023

Related U.S. Application Data

(60) Provisional application No. 62/942,002, filed on Nov. 29, 2019.

(51) Int. Cl.
| | |
|---|---|
| *C07K 14/415* | (2006.01) |
| *A01H 6/20* | (2018.01) |
| *A01H 6/46* | (2018.01) |
| *A01H 6/54* | (2018.01) |

(52) U.S. Cl.
CPC ............. *C07K 14/415* (2013.01); *A01H 6/20* (2018.05); *A01H 6/46* (2018.05); *A01H 6/54* (2018.05)

(58) Field of Classification Search
None
See application file for complete search history.

(56) References Cited

U.S. PATENT DOCUMENTS

| | | | |
|---|---|---|---|
| 11,692,199 B2 * | 7/2023 | Medford ............ | C12N 15/8242 210/602 |
| 2010/0162427 A1 * | 6/2010 | Riechmann .......... | C07K 14/415 800/290 |
| 2016/0046963 A1 | 2/2016 | May et al. | |

FOREIGN PATENT DOCUMENTS

| | | |
|---|---|---|
| WO | WO-2005/121345 A1 | 12/2005 |
| WO | WO-2007/025097 A3 | 7/2007 |
| WO | WO-2013/141680 A1 | 9/2013 |
| WO | WO-2013/176772 A1 | 11/2013 |
| WO | WO-2014/099744 A1 | 6/2014 |
| WO | WO-2014/150624 A1 | 9/2014 |
| WO | WO-2014/099750 A3 | 10/2014 |
| WO | WO-2014/204728 A8 | 7/2015 |
| WO | WO-2014/093595 A9 | 8/2015 |
| WO | WO-2016/205711 A1 | 12/2016 |
| WO | WO-2016/205749 A9 | 1/2017 |
| WO | WO-2018/075900 A1 | 4/2018 |

OTHER PUBLICATIONS

Korma et al, AtMYB41 activates ectopic suberin synthesis and assembly in multiple plant species and cell types 2014, The Plant Journal 80: 216-229 (Year: 2014).*

Giles et al, Inferring Function from Homology, 2017, Bioinformatics: vol. II: Structure, Function, and Applications: 23-38. (Year: 2017) (Year: 2017).*

Guo H et al, Protein tolerance to random amino acid change, 2004, Proceedings of the National Academies of Science, 101:9205-9210. (Year: 2004) (Year: 2004).*

Jain et al, A review of plant leaf fungal diseases and its environment speciation, 2019, Bioengineered 10: 409-424 (Year: 2019).*

Chen et al, Identification, cloning and characterization of R2R3-MYB gene family in canola (*Brassica napus* L.) identify a novel member modulating ROS accumulation and hypersensitive-like cell death, 2016, DNA Research 23: 101-114 (Year: 2016).*

Uniprot Accession: A0A142BX61_BRANA, 2016, Myb41, Canola, https://www.uniprot.org/uniprotkb/A0A142BX61/entry (Year: 2016).*

Allen et al 2014, Outlooks on Pest Management 25: 167-174 (Year: 2014).*

Chen et al, 2016, DNA Research 23(2): 101-114 (Year: 2016).*

(Continued)

*Primary Examiner* — Brent T Page
*Assistant Examiner* — Aleksandar Radosavljevic
(74) *Attorney, Agent, or Firm* — MARSHALL, GERSTEIN & BORUN LLP

(57) ABSTRACT

The present invention relates to a method of conferring or increasing resistance against fungal pathogens in plants, plant parts, and/or plant cells. To this end the invention focuses on facilitating or increasing the production and/or accumulation of a Myb41-type transcription factor (Myb41), fragment or homolog thereof in a plant, plant part and/or plant cell compared to corresponding wild type plants, wild type plant parts and/or wild type plant cells. The invention also relates to plants, plant parts, and/or plant cells having an increased resistance against fungal pathogens and to material and methods to create or use such plants plant parts or to produce products therefrom.

4 Claims, 9 Drawing Sheets

Specification includes a Sequence Listing.

(56) References Cited

OTHER PUBLICATIONS

Wang et al, 2021, BMC Plant Biology 21:328 (Year: 2021).*
Dubos et al, 2010, Trends in Plant Science, 15 (10): 573-581 (Year: 2010).*
Cominelli, et al., "Over?expression of the *Arabidopsis* AtMYB41 gene alters cell expansion and leaf surface permeability", The Plant Journal, vol. 53, Issue 1, Sep. 14, 2007, pp. 53-64.
Dubos, et al., "MYB transcription factors in *Arabidopsis*", Trends in Plant Science, vol. 15, Issue 10, Oct. 2010, pp. 573-581.
Gall, et al., "Cell Wall Metabolism in Response to Abiotic Stress", Plants, vol. 4, Issue 1, Feb. 16, 2015, pp. 112-166.
Hoang, et al., "Phosphorylation by AtMPK6 is required for the biological function of AtMYB41 in *Arabidopsis*", Biochemical and Biophysical Research Communications, vol. 422, Issue 1, May 25, 2012, pp. 181-186.
Kosma, et al., "AtMYB41 activates ectopic suberin synthesis and assembly in multiple plant species and cell types", The Plant Journal, vol. 80, Issue 2, Jul. 25, 2014, pp. 216-229.
Lippold, et al., "AtMyb41 Regulates Transcriptional and Metabolic Responses to Osmotic Stress in *Arabidopsis*", Plant Physiology, vol. 149, Issue 4, Feb. 11, 2009, pp. 1761-1772.
International Application No. PCT/EP2020/083329, International Search Report and Written Opinion, mailed Mar. 1, 2021.

* cited by examiner 0,6%     2,0%     7,0%     18,0%     42,0%     78,5%

```
201 - 282

****   *   *    * *            *    *          *      * *
* ***  ***   **  *   *          *   *    *    *    *      * ***
** *** *** ** *    * *         *   *    *    * * *    ** ****
******* ***  *  * *  *   *  *  *  *   * *   ** **** *** *****
*********  ****** ** *** *** *** ** * **** *** **** ** *****
********* ****** **** *** ****  *** **** *** **** *** *****
*************************************************************
*************************************************************
*************************************************************
*************************************************************
*************************************************************

QAETSTVPTNYETSSLEPMNARLDDVGLADVLPPLSESFDLDSLMSTPMSSPRQNSIEAETNSSTFFDEGIPEDFILDDFMF  SEQ ID NO: 2
QAECTT-PSNDETSSFEPMNARL-DVGPSDVLPPLSESFDLDSLMSTPMSSPQQNSIEAEANSSSFFDEGIPDNFIFDDFMF  SEQ ID NO: 5
ALSLSSPTTKNIKNYLDLIKKKVDEMSLAYAVHSDNNALECQLVLPWLVYT-GRDNE-RDTFPDL-E-EFDEDLTLAEIFL   SEQ ID NO: 10
NGHTPARVDGEDN--WNSQDNQMGLHAHEAKRTDMRLGMNYEKMIRR-NA-AN-TDTH--S-CKTEI-LRLAAS-DIESHLG  SEQ ID NO: 11
SDRSNGSAACYHEGH VTEQFTAKKKHNHKLTDTQARPKGAA I-T-K--RNRMKEVKSQ-GFN--KKM-N RVISAKAPSN   SEQ ID NO: 12
TNAM RV CIFQ IG TQLGR   SVL  GN--IK IKHRTKEH   N-ASLELQ-D-Q- TCMS--EHLNWAQ TEVRNNPYYR  SEQ ID NO: 13
TTN IY NSSV N QVHRS     TNS  W-RDY NTSTISSL PGK SN    VNE-L CGVDG GVPR NT LL PMP LGV    SEQ ID NO: 14
    P YT AQ- -V   VY   R      N I  MPSGN IKH N N YY    NM      SQ S Y                    SEQ ID NO: 15
      ESQ K        I   S      P K      T TP NN W        T       S   C                    SEQ ID NO: 16
        I S              Q                         Y                                     SEQ ID NO: 17
        Q T                                                                              SEQ ID NO: 18
```

INCREASING RESISTANCE AGAINST FUNGAL INFECTIONS IN PLANTS

CROSS-REFERENCE TO RELATED APPLICATIONS

This is the U.S. national phase of International Application No. PCT/EP2020/083329, filed Nov. 25, 2020, which claims the benefit of U.S. Provisional Patent Application No. 62/942,002, filed on Nov. 29, 2019.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "182122A_SubSeglisting", which was created on Aug. 20, 2024 and is 98,262 bytes in size. The subject matter of the Sequence Listing is incorporated herein in its entirety by reference.

SUMMARY OF THE INVENTION

The present invention relates to a method of conferring or increasing resistance against fungal pathogens in plants, plant parts, and/or plant cells. To this end the invention focuses on facilitating or increasing the production and/or accumulation of a Myb41-type transcription factor (Myb41), fragment or homolog thereof in a plant, plant part and/or plant cell compared to corresponding wild type plants, wild type plant parts and/or wild type plant cells. The invention also relates to plants, plant parts, and/or plant cells having an increased resistance against fungal pathogens and to material and methods to create or use such plants plant parts or to produce products therefrom.

BACKGROUND OF THE INVENTION

The cultivation of agricultural crop plants serves mainly for the production of foodstuffs for humans and animals. Monocultures in particular, which are routine nowadays, are highly susceptible to an epidemic-like spread of diseases. The result is markedly reduced yields. To date, the pathogenic organisms have been controlled mainly by using pesticides. Nowadays, the possibility of directly modifying the genetic disposition of a plant or pathogen is also open to man. Alternatively, natural occurring fungicides produced by the plants after fungal infection can be synthesized and applied to the plants. Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host is seriously hampered in development or dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is mostly specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant. To counteract plants have developed physical barriers, such as wax layers, and chemical compounds having antifungal effects to inhibit spore germination, hyphal growth or penetration.

The soybean rust fungus *Phakopsora pachyrhizi* directly penetrates through the cuticle and the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyll cell. During the penetration process the plasma membrane of the penetrated mesophyll cell stays intact.

The initial step of pathogenesis of Asian soybean rust disease is the initial penetration of the fungus through the plant cuticule into the epidermal cell. The plant cuticle is an extracellular hydrophobic layer that covers the aerial epidermis and that consists of two major components, the polymer cutin and cuticular waxes (for review about plant cuticle see Yeats T H, Rose J K. The formation and function of plant cuticles. Plant Physiol. 2013; 163(1):5-20). The cuticle provides protection against desiccation, external environmental stresses and pathogens. For example it has been shown that lower cutin amounts in tomato "cd" mutants are associated with increased susceptibility to *Botrytis cinerea* (Isaacson et al., 2009). To facilitate penetration through the cuticle many fungal pathogens secrete enzymes to degrade or weaken the cuticle, such as e.g. cutinases, a class of small, nonspecific esterases that hydrolyze the cutin polymer.

In addition to cutin also the epicuticular waxes play an important role in pathogen development and defense. For example it has been shown that the "inhibitor of rust tube germination1" (irg1) mutant of *M. truncatula* showed less epicuticular wax crystals on the abaxial leaf surface and a strong decrease in wax primary alcohol groups. This surface alteration led to an increased resistance against the fungal pathogens *Phakopsora pachyrhizi, Puccinia emaculata* and the anthracnose fungus *C. trifolii* (Uppalapati et al., 2012). The authors found that IRG1 codes for a Cys(2)His(2) zinc finger transcription factor also called PALM1.

Biotrophic phytopathogenic fungi depend for their nutrition on the metabolism of living cells of the plants. This type of fungi belong to the group of biotrophic fungi, like many rust fungi, powdery mildew fungi or oomycete pathogens like the genus *Phytophthora* or *Peronospora*. Necrotrophic phytopathogenic fungi depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic. After the penetration, the fungus switches to an obligatory biotrophic lifestyle. The subgroup of the biotrophic fungal pathogens which follows essentially such an infection strategy are heminecrotrohic.

Soybean rust has become increasingly important in recent times. The disease is caused by the biotrophic rusts *Phakopsora pachyrhizi* (Sydow) and *Phakopsora meibomiae* (Arthur). They both belong to the class Basidiomycota, order Uredinales, family Phakopsoraceae. Both rusts infect a wide spectrum of leguminosic host plants.

*P. pachyrhizi* is the more aggressive pathogen on soybean (*Glycine max*), and is therefore, at least currently, of great importance for agriculture. *P. pachyrhizi* can be found in nearly all tropical and subtropical soybean growing regions of the world. *P. pachyrhizi* is capable of infecting 31 species from 17 families of the Leguminosae in nature and is capable of growing on further 60 species in controlled conditions (Sinclair et al. (eds.), Proceedings of the rust workshop (1995), National Soybeana Research Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soybean plants with resistance to the entire spectrum of the isolates are not available. When searching for resistant soybean accessions, six dominant R genes of the NBS-LRR family, which mediate resistance of soybean to *P. pachyrhizi*, were discovered. The resistance they conferred was lost rapidly, as *P. pachyrhizi* develops new virulent races.

In recent years, fungal diseases, e.g. soybean rust, became more important in agricultural production. There was, therefore, a demand in the prior art for developing methods to control fungi and to provide plants that resist fungal diseases.

A lot of research has been performed on powdery and downy mildew infecting the epidermal layer of plants. However, the problem to cope with soybean rust, which infects the mesophyll or with *Fusarium* fungi that infect inaccessible inner tissues remains unsolved.

The object of the present invention is inter alia to provide a method of increasing resistance against fungal pathogens, preferably against fungal pathogens of the family Phakopsoraceae, more preferably against fungal pathogens of the genus *Phakopsora*, most preferably against *Phakopsora pachyrhizi* (Sydow) and/or *Phakopsora meibomiae* (Arthur), also known as soybean rust.

Surprisingly, we found that fungal pathogens, in particular of the family Phakopsoraceae, for example soybean rust, can be controlled by expression of the Myb41 protein, which initially has been identified as a repressor of cutin biosynthesis (Cominelli et al. (2008) Over-expression of the *Arabidopsis* AtMYB41 gene alters cell expansion and leaf surface permeability. Plant J. 53(1):53-64). Cominelli et al. had found that overexpression of AtMYB41 resulted in a dwarf phenotype similar to that exhibited by some mutants that affect cuticle biosynthesis.

The MYB superfamily of transcription factors is a large and functionally diverse protein family that can be found in all eukaryotes. In plants, the MYB family has selectively expanded. For example in *Arabidopsis* there 196 Myb transcription factor homologs can be found, which belong to 4 different families (for a comprehensive review about Myb transcription factors in *Arabidopsis* see Dubos et al. (2010), Trends in Plant Science, Vol. 15, No. 10; 573-581).

The Myb41 protein described in this invention belongs to the R2R3-MYB family, which consist of 126 members in *Arabidopsis*. R2R3-MYB genes are reported to be involved in many divergent regulatory networks controlling development, metabolism and responses to biotic and abiotic stresses.

In *Arabidopsis* AtMYB41 is expressed at high levels in response to drought, ABA and salt treatments, suggesting a possible role in stress responses. Transgenic lines overexpressing this transcription factor in *Arabidopsis* showed a pleiotropic phenotype (dwarf appearance) similar to that exhibited by some mutants that affect cuticle biosynthesis (Cominelli et al. (2008) Over-expression of the *Arabidopsis* AtMYB41 gene alters cell expansion and leaf surface permeability. Plant J. 53(1):53-64). Nevertheless, the real cause of the phenotypes was not analyzed in this publication. Further characterization of AtMyb41-overexpressing lines by transcriptome and metabolome analysis showed that AtMyb41 is involved in several cellular processes, including control of primary metabolism and negative regulation of short-term transcriptional responses to osmotic stress (Lippold et al. AtMyb41 regulates transcriptional and metabolic responses to osmotic stress in *Arabidopsis*. Plant Physiol. 149:1761-1772(2009)). By further evaluating the role of Myb41 in tolerance to salt and desiccation it turned out that is regulated by phosphorylation of Ser251 by the mitogen-activated protein kinase MPK6; the phosphorylation of MYB41 by MPK6 is required for the biological function of MYB41 in salt tolerance (Hoang et al., Biochem Biophys Res Commun. 2012 May; 422(1) 181-186).

Recently the molecular mechanism of the overexpression of AtMyb41 gene has been linked to the synthesis of Suberin in leaves. (Kosma et al. AtMYB41 activates ectopic suberin synthesis and assembly in multiple plant species and cell types. Plant J. 80:216-229(2014) Suberin is a lipid and phenolic cell wall heteropolymer found in the roots and vascular tissues of all plants. Suberin plays a critical role in plant water relations and in protecting plants from biotic and abiotic stresses. Kosma at al. showed that the expression of AtMYB41 can activate all the steps necessary for suberin synthesis and deposition of cell wall-associated suberin-like lamellae. Therefore overexpression of AtMYB41 will increase suberin, lignin and phenylpropanoid biosynthetic gene transcripts and will elevate amounts of monolignols in leaves resulting in the formation of suberin-like lamellae in both epidermal and mesophyll cells of leaves.

The formation of suberin-lamellae in leaves has never been linked to increased resistance to fungal pathogens. Therefore it was surprising to find an increased resistance to *Phakopsora pachyrhizi* after overexpression of AtMyb41 in soybean. Also, there appear to be distinct responses to stressors for different species as described by Le Gall et al. (Cell Wall Metabolism in Response to Abiotic Stress. Plants 2015, 112-166) for the difference in salt response in rosids and *Arabidopsis*. It is thus not possible to extrapolate stress responses found for example in *Arabidopsis* to other plant species.

SUMMARY OF THE INVENTION

The present invention accordingly provides a method for conferring or increasing fungal resistance in a plant, a plant part, or a plant cell wherein the method comprises the step of increasing the production and/or accumulation of Myb41 in the plant, plant part, or plant cell in comparison to a respective wild type plant, wild type plant part, or wild type plant cell.

Further provided is a method of conferring or increasing fungal resistance in a plant, a plant part, or a plant cell, wherein the method comprises increasing the expression and/or biological activity of a Myb41 protein in the plant, plant part, or plant cell in comparison to a respective wild type plant, wild type plant part, or wild type plant cell, wherein said Myb41 protein is encoded by (i) an exogenous nucleic acid having at least 70% identity, at least 80% identity, at least 90% identity, at least 95% identity with SEQ ID NO. 1, or a functional fragment thereof or a splice variant thereof;

(ii) an exogenous nucleic acid encoding a protein having at least 70% identity, at least 80% identity, at least 90% identity, at least 95% identity with SEQ ID NO. 2 or 5, or a functional fragment thereof;

(iii) an exogenous nucleic acid capable of hybridizing under stringent conditions with a complementary sequence of any of the nucleic acids according to (i) or (ii); or (iv) an exogenous nucleic acid encoding the same Myb41 protein as the nucleic acids of (i) to (iii) above, but differing from the nucleic acids of (i) to (iii) above due to the degeneracy of the genetic code.

The invention also provides a recombinant vector construct comprising a nucleic acid encoding a Myb41 protein of the present invention.

Further provided is a genetically modified plant, genetically modified plant part, or genetically modified plant cell transformed with one or more recombinant vector construct(s) of the present invention.

The invention also provides a crop plant, crop plant part or crop plant cell overexpressing a Myb41 protein of the present invention.

Also, the invention provides a method for the production of a genetically modified crop plant, genetically modified crop plant part, or genetically modified crop plant cell having increased fungal resistance compared to a respective wild type plant, plant part or plant cell, comprising (a) introducing an exogenous nucleic acid encoding a Myb41 protein into a plant, a plant part, or a plant cell, (b) generating a genetically modified plant, genetically modified plant part, or genetically modified plant cell from the plant, plant part or plant cell; and (c) expressing the Myb41 protein in the genetically modified plant, genetically modified plant part, or genetically modified plant cell from the plant.

According to an aspect of the invention a Myb41 protein or of a nucleic acid encoding a Myb41 protein is used to increase fungal resistance in a plant.

The invention also provides method of controlling a fungus in a field, preferably by reducing or delaying infection of plants in a field and/or reducing or delaying emission of fungal spores from the field, comprising the step of (a) planting seed from any plant of the present invention and/or (b) increasing suberin-lamellae formation in the plants.

And the invention provides a harvestable part of a plant of the present invention, wherein the harvestable part of the plant comprises an exogenous nucleic acid encoding a Myb41 protein of the present invention.

The invention also provides a product derived from a plant of the present invention, from a plant producible by the method of the present invention or from the harvestable part of the plant of the present invention, wherein the product comprises an exogenous nucleic acid encoding the Myb41 protein and/or the Myb41 protein of the present invention. Preferred products according to the invention are fruit, more preferably seed, and products derived from such fruit, preferably dried fruit and dried fruit pieces, meal and oil. Most preferred according to the invention are soybeans, soybean meal and soybean oil.

The invention also provides a method for the production of a product, comprising a) growing a plant of the present invention or obtainable by the method of the present invention and b) producing said product from or by the plant and/or part, preferably seeds, of the plant, wherein the product comprises an exogenous nucleic acid encoding the Myb41 protein and/or the Myb41 protein of the present invention.

And the invention provides a method of assaying a plant for resistance to a fungus, comprising the screening for the overexpression of a Myb41 gene in a cell of said plant. In the context of the present invention, the fungal resistance is envisaged to comprise resistance against a biotrophic, hemibiotrophic or heminecrotrophic fungus, preferably a rust fungus, downy mildew, powdery mildew, leaf spot, late blight, *fusarium* and/or *septoria*.

Also in the context of the present invention the plant is preferably selected from the group consisting of members of the taxonomic family Fabaceae, Brassicaceae and Poaceae, most preferably soy.

The invention also provides a method for breeding a fungal resistant crop plant comprising (a) crossing the plant of the present invention or the plant obtainable by the method of the present invention with a second plant;

(b) obtaining seed from the cross of step (a);

(c) planting said seeds and growing the seeds to plants; and (d) selecting from said plants such plants as express Myb41 protein of the present invention.

The objects of the present invention, as outlined above, are primarily achieved by the subject-matter of the independent claims. Preferred embodiments of the invention are defined by the subject matter of the dependent claims or are described in more detail hereinafter.

7 matic scale for assessment of soybean rust severity. *Fitopa-tologia Brasileira* 31:063-068. 2006.).

Figure 2:
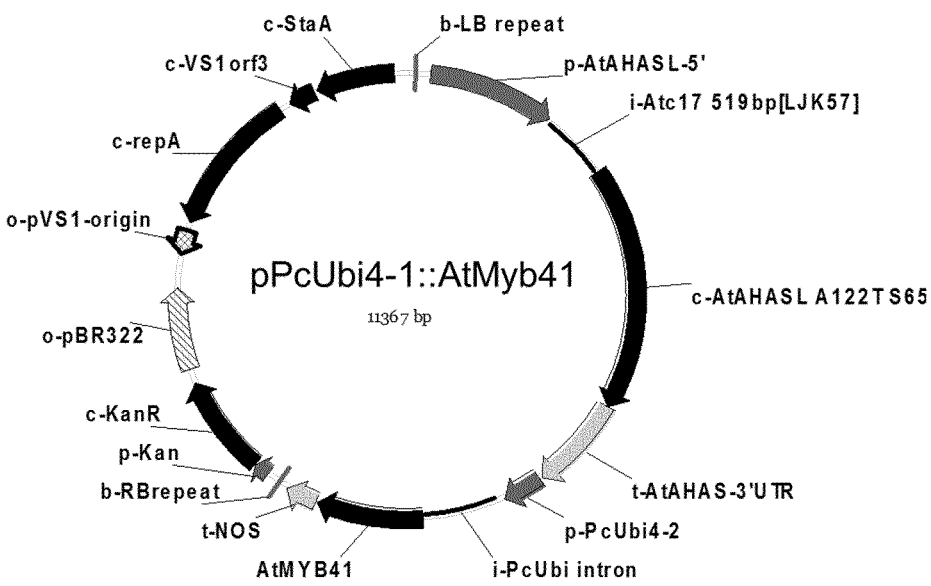

FIG. 2 shows the schematic illustration of the plant transformation vector harboring the fragment of the Myb41 DNA under control of the parsley ubiquitin promoter as used in an example of this invention.

Figure 3:
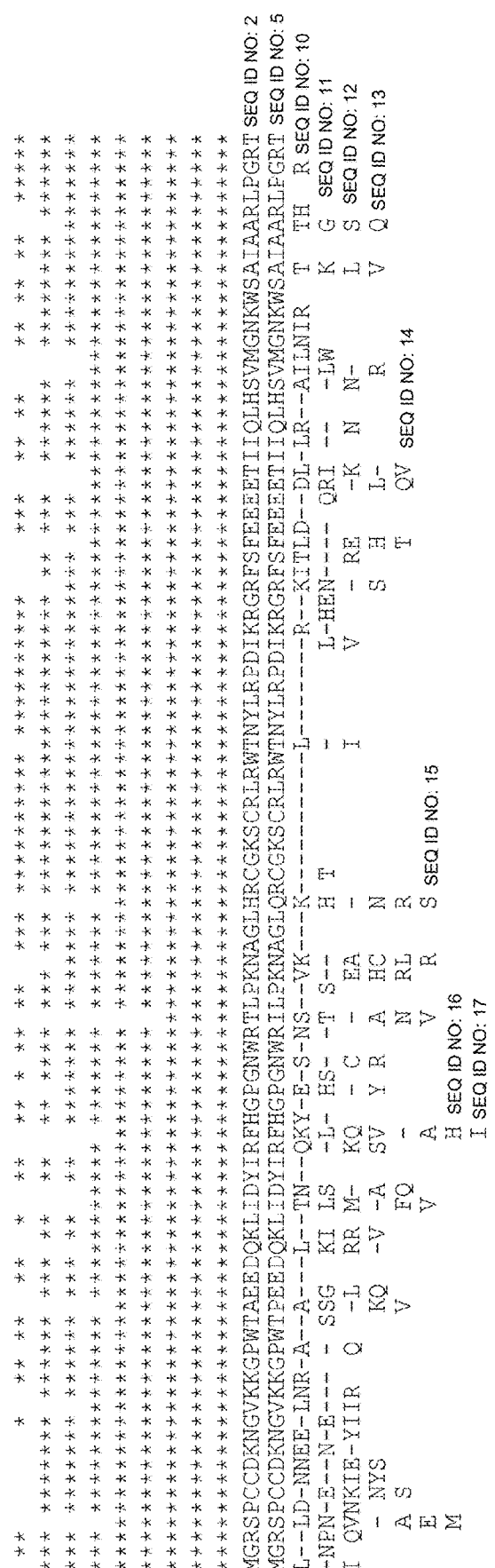
Figure 3:
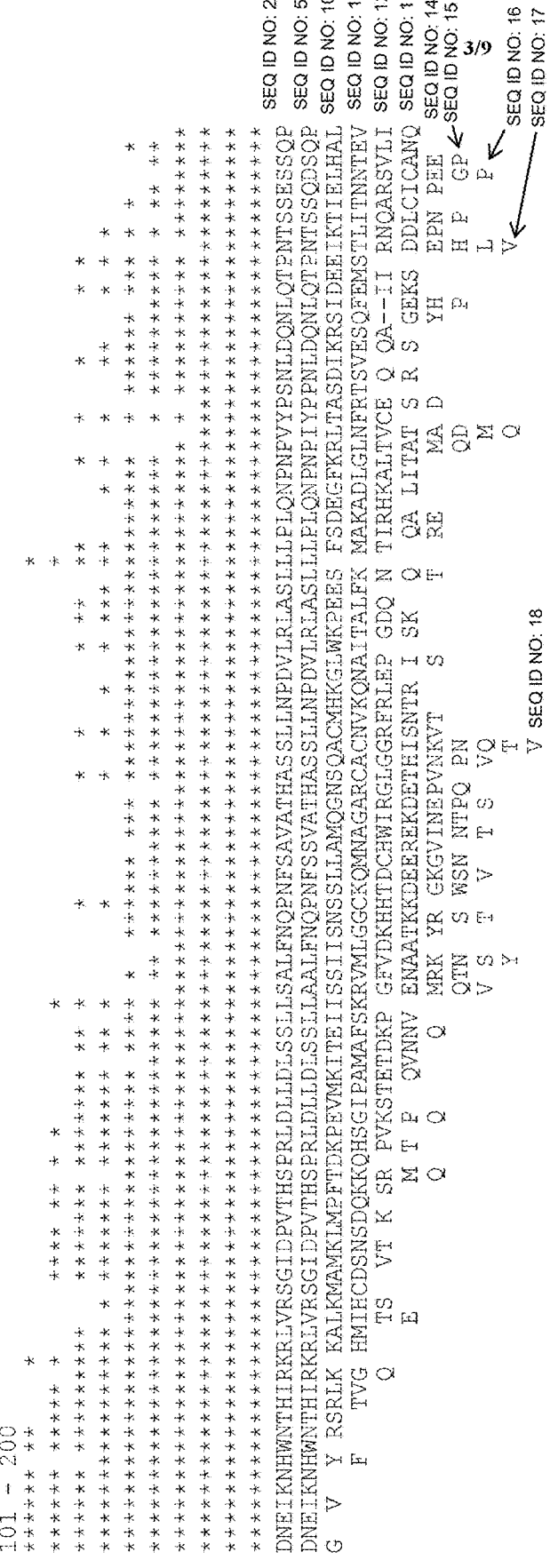

FIG. 3 shows a plot of positional amino acid conservation. Per columns: The number of stars indicates the degree of conservation (more stars indicate higher degree of conservation); the first letter/"-" below the stars is the respective amino acid (or alignment gap) encountered in SEQ ID NO. 2; all letters/"-" below indicate, in decreasing order of frequency, the amino acids, or, indicated by "–", the alignment gaps encountered in homologous Myb41 genes.

Figure 4:
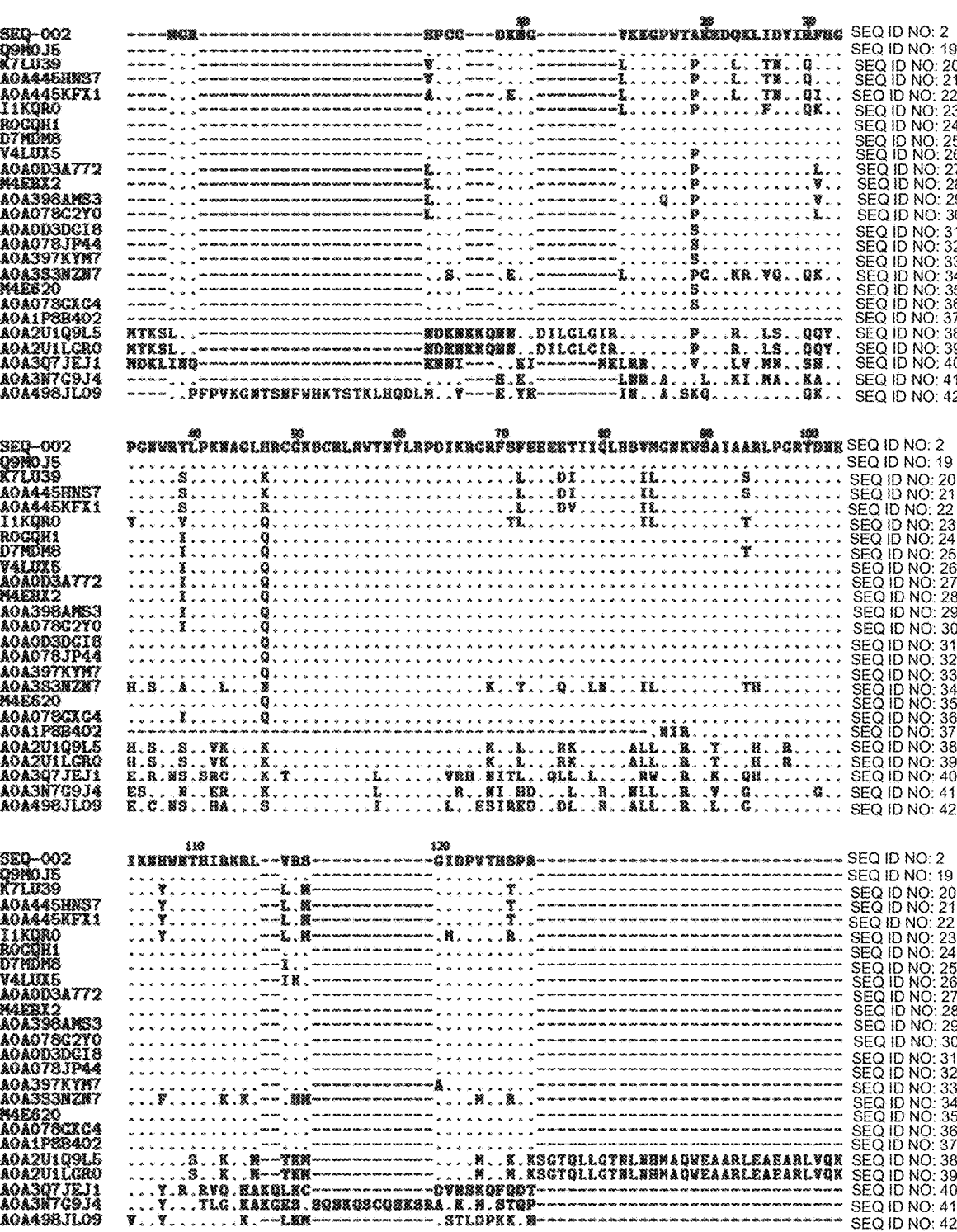
Figure 4:
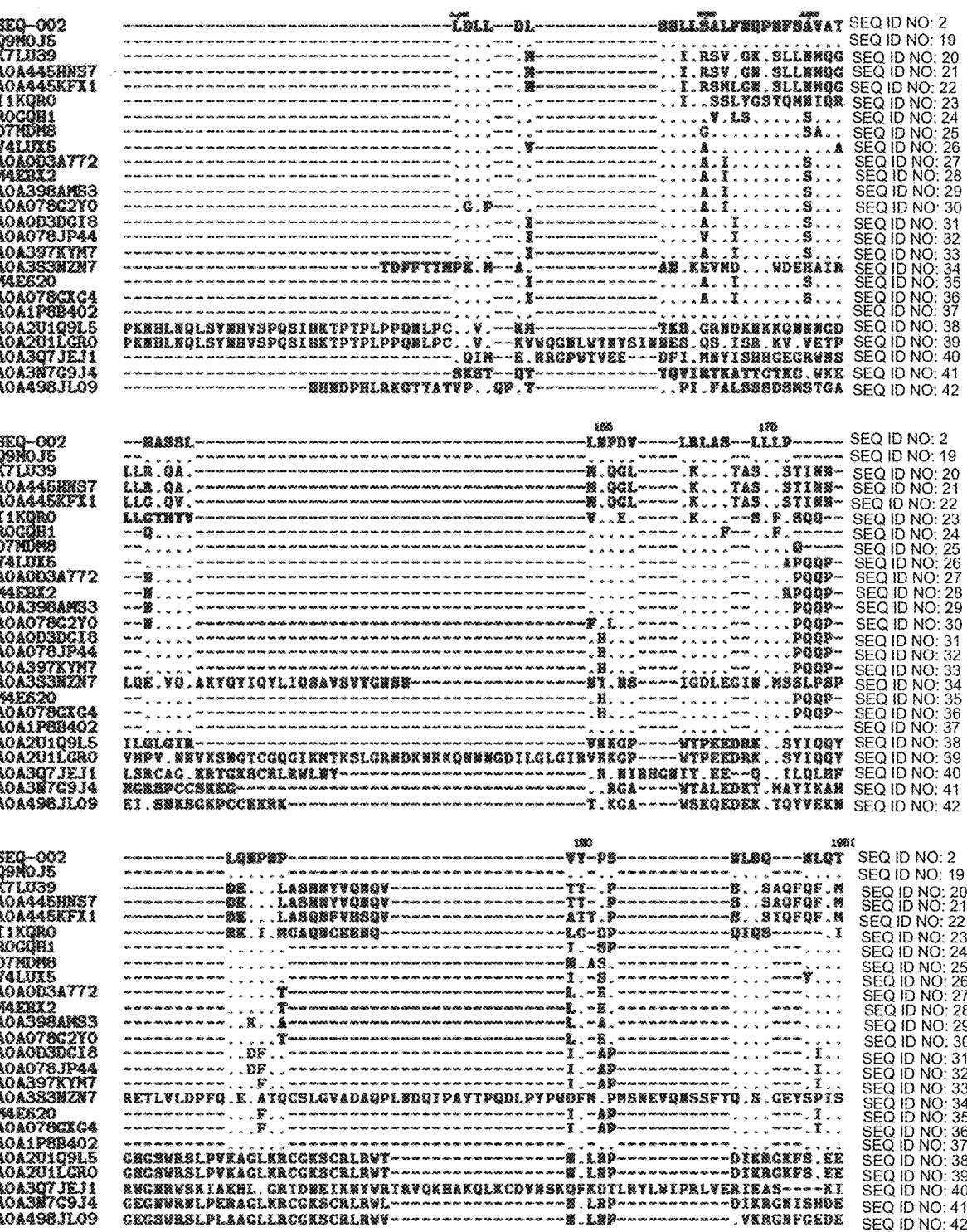
Figure 4:
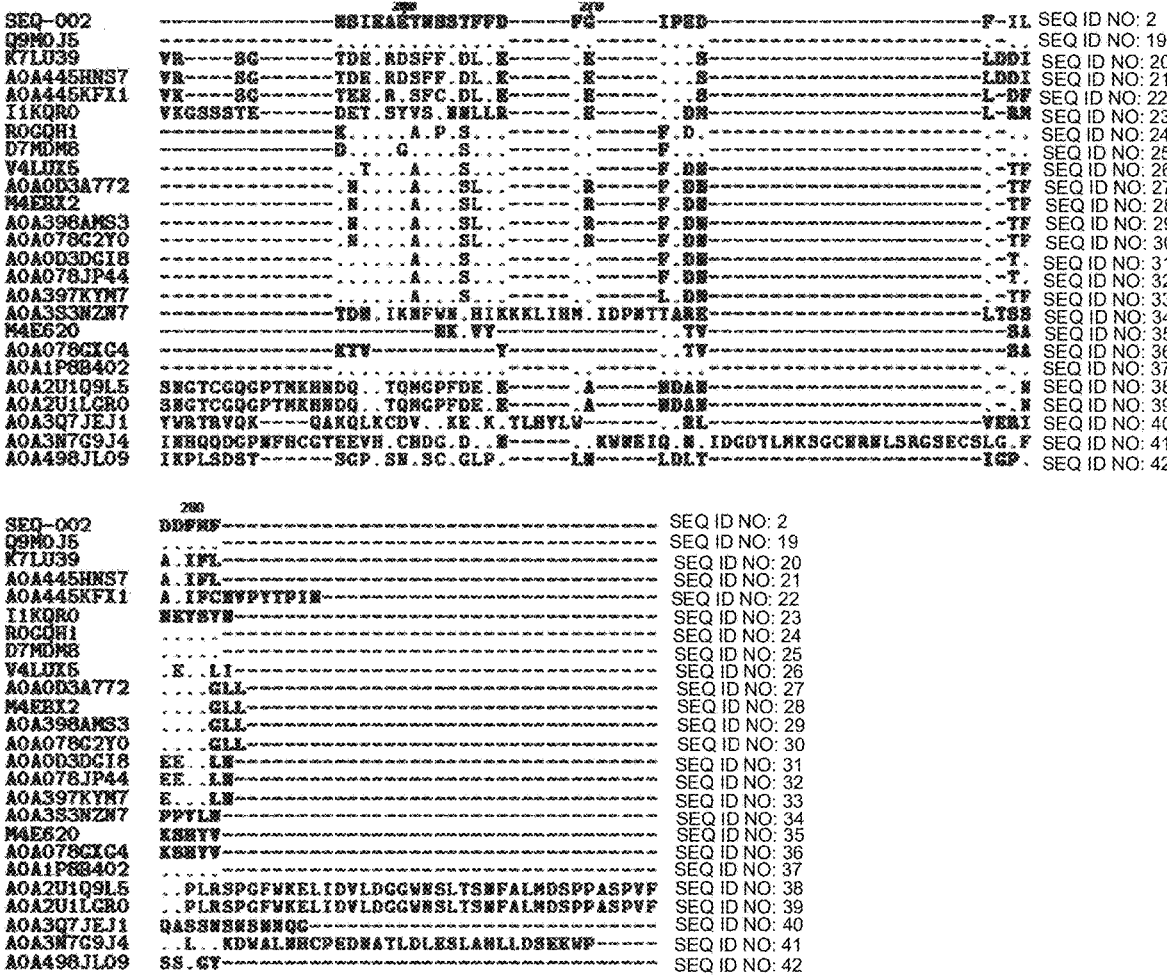

FIG. 4 shows a multiple alignment of a Myb41 sequence of the present invention (SEQ ID NO. 2) and the corresponding sequences of homologs identified by their Uniprot identifier. The amino acid sequence is given only for the top sequence SEQ ID NO. 2, for every other sequence per position only the differing amino acids or "–" for a gap are indicated ("." denotes "same amino acid as in top sequence").

Figure 5:
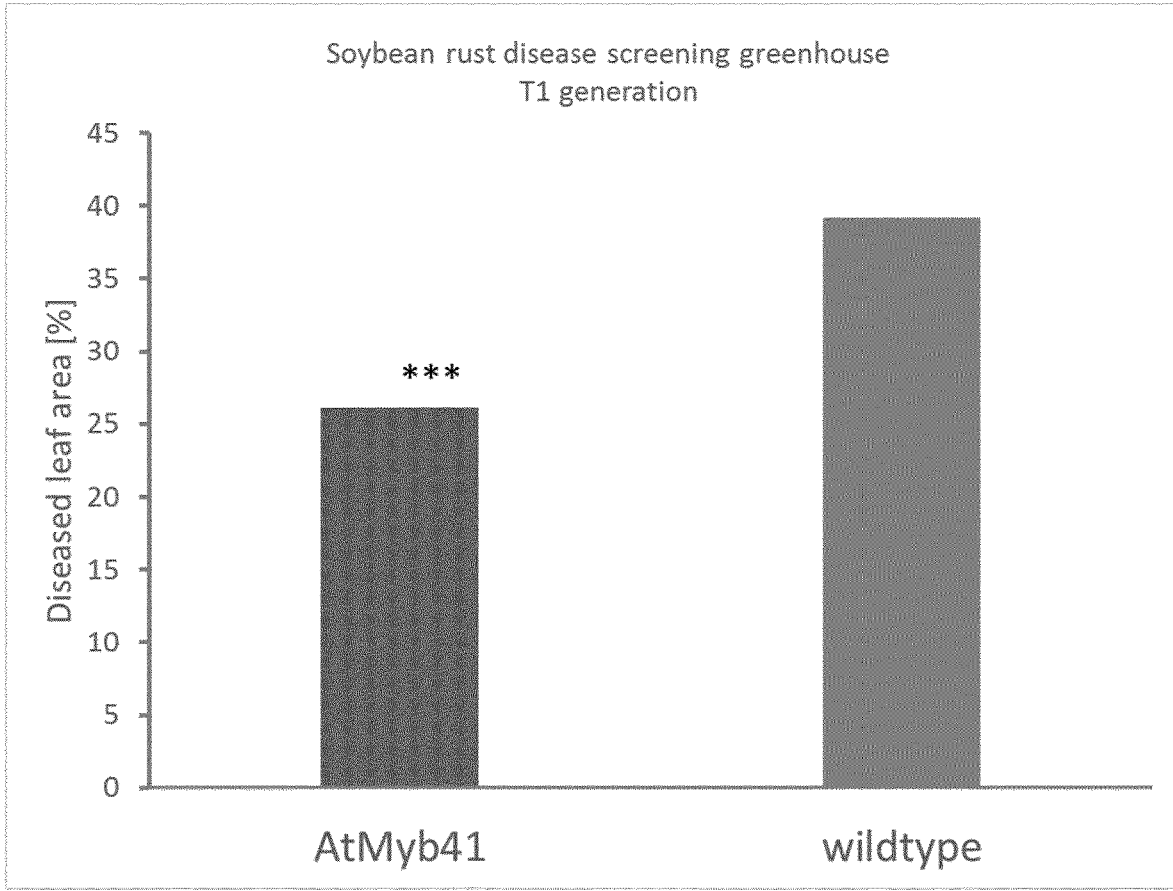

FIG. 5 shows the result of the scoring of 107 transgenic soy plants derived from 9 independent transformation events (11-12 plants per event) expressing Myb41 overexpression vector construct. The experiment was performed using plants of the T1 generation. Transgenicity of the plants was checked by PCR. Non-transgenic plants were discarded. T1 soybean plants harboring the Myb41 expression cassette were inoculated with spores of *Phakopsora pachyrhizi*. The expression of the Myb41 gene was checked by RT-PCR. The evaluation of the diseased leaf area on all leaves was performed 14 days after inoculation. The average of the percentage of the leaf area showing fungal colonies or strong yellowing/browning on all leaves was considered as diseased leaf area. At all 107 soybean T1 plants expressing the Myb41 (expression checked by RT-PCR) were evaluated in parallel to non-transgenic control plants. The average of the diseased leaf area of Myb41 expressing plants and wild type control plants is shown in FIG. 5. Overexpression of Myb41 significantly (***: p<0.001) reduces the diseased leaf area in comparison to non-transgenic control plants by 33.5%.

8

The technical teaching of the invention is expressed herein using the means of language, in particular by use of scientific and technical terms. However, the skilled person understands that the means of language, detailed and precise as they may be, can only approximate the full content of the technical teaching, if only because there are multiple ways of expressing a teaching, each necessarily failing to completely express all conceptual connections, as each expression necessarily must come to an end. With this in mind the skilled person understands that the subject matter of the invention is the sum of the individual technical concepts signified herein or expressed in a pars-pro-toto way by the innate constrains of a written description. In particular, the skilled person will understand that the signification of individual technical concepts is done herein as an abbreviation of spelling out each possible combination of concepts as far as technically sensible, such that for example the disclosure of three concepts or embodiments A, B and C are a shorthand notation of the concepts A+B, A+C, B+C, A+B+C.

As used herein, terms in the singular and the singular forms like "a", "an" and "the" include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant or plants derived therefrom by crossing; use of the term "a nucleic acid" optionally includes, as a practical matter, many copies of that nucleic acid molecule; similarly, the term "probe" optionally (and typically) encompasses many similar or identical probe molecules. Also as used herein, the word "comprising" or variations such as "comprises" or "comprising" will be understood to imply the inclusion of a stated element, integer or step, or group of elements, integers or steps, but not the exclusion of any other element, integer or step, or group of elements, integers or steps.

As used herein, the term "and/or" refers to and encompasses any and all possible combinations of one or more of the associated listed items, as well as the lack of combinations when interpreted in the alternative ("or"). The term "comprising" also encompasses the term "consisting of".

The term "about", when used in reference to a measurable value, for example an amount of mass, dose, time, temperature, sequence identity and the like, refers to a variation of

BRIEF DESCRIPTION OF SEQUENCES

| SEQ ID NO. | Description |
| --- | --- |
| 1 | preferred artificial nucleic acid encoding a Myb41 protein of SEQ ID NO. 2 |
| 2 | Arabidopsis thaliana Myb41 protein |
| 3 | Genomic nucleic acid sequence coding for SEQ ID NO. 2 |
| 4 | artificial minimal consensus sequence |
| 5 | Artificial short Myb41 protein wherein each amino acid in the sequence of SEQ ID NO. 2 is replaced by the most frequent amino acid (or gap) encountered in the homologs |
| 6 | Artificial phosphomimetic mutant of SEQ ID NO. 2 |
| 7 | Alternative phosphomimetic mutant of SEQ ID NO. 2 |
| 8 | Artificial phosphomimetic mutant of SEQ ID NO. 5 |
| 9 | Alternative phosphomimetic mutant of SEQ ID NO. 5 |

DETAILED DESCRIPTION OF THE INVENTION

The current invention is focused on the application of Myb41 for the protection of plants against fungal infection and progress of such infective diseases.

±0.1%, 0.25%, 0.5%, 0.75%, 1%, 2%, 3%, 4%, 5%, 6%, 7%, 8%, 9%, 10%, 15% or even 20% of the specified value as well as the specified value. Thus, if a given composition is described as comprising "about 50%x," it is to be understood that, in some embodiments, the composition comprises 50%x whilst in other embodiments it may comprise anywhere from 40% to 60%x (i.e., 50%±10%).

As used herein, the term "gene" refers to a biochemical information which, when materialised in a nucleic acid, can be transcribed into a gene product, i.e. a further nucleic acid, preferably an RNA, and preferably also can be translated into a peptide or polypeptide. The term is thus also used to indicate the section of a nucleic acid resembling said information and to the sequence of such nucleic acid (herein also termed "gene sequence").

Also as used herein, the term "allele" refers to a variation of a gene characterized by one or more specific differences in the gene sequence compared to the wild type gene sequence, regardless of the presence of other sequence differences. Alleles or nucleotide sequence variants of the invention have at least, in increasing order of preference, 30%, 40%, 50%, 60%, 70%, 71%, 72%, 73%, 74%, 75%, 76%, 77%, 78%, 79%, 80%, 81%-84%, 85%, 86%, 87%, 88%, 89%, 90%, 91%, 92%, 93%, 94%, 95%, 96%, 97%, 98% or 99% nucleotide "sequence identity" to the nucleotide sequence of the wild type gene. Correspondingly, where an "allele" refers to the biochemical information for expressing a peptide or polypeptide, the respective nucleic acid sequence of the allele has at least, in increasing order of preference, 30%, 40%, 50%, 60%, 70%, 71%, 72%, 73%, 74%, 75%, 76%, 77%, 78%, 79%, 80%, 81%-84%, 85%, 86%, 87%, 88%, 89%, 90%, 91%, 92%, 93%, 94%, 95%, 96%, 97%, 98% or 99% amino acid "sequence identity" to the respective wild type peptide or polypeptide.

Mutations or alterations of amino or nucleic acid sequences can be any of substitutions, deletions or insertions; the terms "mutations" or "alterations" also encompass any combination of these. Hereinafter, all three specific ways of mutating are described in more detail by way of reference to amino acid sequence mutations; the corresponding teaching applies to nucleic acid sequences such that "amino acid" is replaced by "nucleotide". "Substitutions" are described by providing the original amino acid followed by the number of the position within the amino acid sequence, followed by the substituted amino acid. For example, the substitution of histidine at position 120 with alanine is designated as "His120Ala" or "H120A".

"Deletions" are described by providing the original amino acid followed by the number of the position within the amino acid sequence, followed by "*" or "-". Accordingly, the deletion of *glycine* at position 150 is designated as "Gly150*", "G150*", "Gly150-" or "G150-". Alternatively, deletions are indicated by e.g. "deletion of D183 and G184".

"Insertions" are described by providing the original amino acid followed by the number of the position within the amino acid sequence, followed by the original amino acid and the additional amino acid. For example, an insertion at position 180 of lysine next to *glycine* would be designated as "Gly180GlyLys" or "G180GK". When more than one amino acid residue is inserted, such as e.g. a Lys and Ala after Gly180 this may be indicated as: Gly180GlyLysAla or G180GKA. In cases where a substitution and an insertion occur at the same position, this may be indicated as S99SD+ S99A or in short S99AD. In cases where an amino acid residue identical to the existing amino acid residue is inserted, it is clear that degeneracy in the nomenclature arises. If for example a *glycine* is inserted after the *glycine* in the above example this would be indicated by G180GG.

Variants comprising multiple alterations are separated by "+", e.g. "Arg170Tyr+Gly195Glu" or "R170Y+G195E" representing a substitution of arginine and *glycine* at positions 170 and 195 with tyrosine and glutamic acid, respectively. Alternatively, multiple alterations may be separated by space or a comma e.g. R170Y G195E or R170Y, G195E respectively.

Where different alterations can be introduced at a position, the different alterations are separated by a comma, e.g. "Arg170Tyr, Glu" represents a substitution of arginine at position 170 with tyrosine or glutamic acid. Alternatively, different alterations or optional substitutions may be indicated in brackets e.g. Arg170[Tyr, Gly] or Arg170{Tyr, Gly} or in short R170[Y,G] or R170{Y, G}.

A special aspect concerning amino acid substitutions are conservative mutations which often appear to have a minimal effect on protein folding resulting in substantially maintained peptide or polypeptide properties of the respective peptide or polypeptide variant compared to the peptide or polypeptide properties of the parent peptide or polypeptide. Conservative mutations are those where one amino acid is exchanged with a similar amino acid. For determination of %-similarity the following applies, which is also in accordance with the BLOSUM62 matrix, which is one of the most used amino acids similarity matrix for database searching and sequence alignments:

Amino acid A is similar to amino acids S
Amino acid D is similar to amino acids E, N
Amino acid E is similar to amino acids D, K and Q
Amino acid F is similar to amino acids W, Y
Amino acid H is similar to amino acids N, Y
Amino acid I is similar to amino acids L, M and V
Amino acid K is similar to amino acids E, Q and R
Amino acid L is similar to amino acids I, M and V
Amino acid M is similar to amino acids I, L and V
Amino acid N is similar to amino acids D, H and S
Amino acid Q is similar to amino acids E, K and R
Amino acid R is similar to amino acids K and Q
Amino acid S is similar to amino acids A, N and T
Amino acid T is similar to amino acids S
Amino acid V is similar to amino acids I, L and M
Amino acid W is similar to amino acids F and Y
Amino acid Y is similar to amino acids F, H and W Conservative amino acid substitutions may occur over the full length of the sequence of a polypeptide sequence of a functional protein such as a peptide or polypeptide. Preferably such mutations are not pertaining the functional domains of a peptide or polypeptide. According to the present invention, a Myb41 gene is a gene coding for a Myb41 polypeptide.

A Myb41 protein of the present invention preferably differs, in an alignment to SEQ ID NO.2, at 3 or less, more preferably at 2 or less, even more preferably at 1 and even more preferably at 0 positions from the respective amino acid of SEQ ID NO. 2 at any of the positions 89, 90, 92, 93, 96, 97, 99, 100, 102, 103, 105, 106, 108, 114 and 170, more preferably at 3 or less, even more preferably at 2 or less, even more preferably at 1 and even more preferably 0 positions from the respective amino acid of SEQ ID NO.2 at the positions 15, 17, 21, 22, 25, 28, 29, 33, 37, 40, 44, 45, 46, 48, 50, 51, 52, 53, 54, 55, 56, 57, 59, 60, 61, 62, 63, 64, 74, 78, 81, 82, 86, 87, 89, 90, 92, 93, 96, 97, 99, 100, 101, 102, 103, 104, 105, 106, 108, 109, 114 and 170, more preferably at 3 or less, even more preferably at 2 or less, even more preferably at 1 and even more preferably 0 positions from the respective amino acid of SEQ ID NO. 2 at the positions 2, 15, 17, 18, 21, 22, 25, 28, 29, 33, 35, 37, 40, 41, 44, 45, 46, 48, 49, 50, 51, 52, 53, 54, 55, 56, 57, 59, 60, 61, 62, 63, 64, 67, 68, 74, 75, 78, 81, 82, 86, 87, 89, 90, 92, 93, 96, 97, 98, 99, 100, 101, 102, 103, 104, 105, 106, 108, 109, 110, 111, 112, 114, 123, 125, 128 and 170, or, as long as the amino acids at positions 89, 90, 92, 93, 96, 97, 99, 100, 102, 103, 105, 106, 108, 114 and 170 of SEQ ID NO. 2 are conserved, more preferably at 5 or less, even more preferably at 4 or less, even more preferably at 3 or less, even more preferably at 2 or less, even more preferably at 1 and even more preferably 0 positions from the respective amino acid of SEQ ID NO. 2 at the positions 2, 3, 5, 6, 7, 8, 9, 10, 11, 13, 14, 15, 16, 17, 18, 20, 21, 22, 24, 25, 28, 29, 32, 33, 35, 37, 38, 40, 41, 44, 45, 46, 48, 49, 50, 51, 52, 53, 54, 55, 56, 57, 58, 59, 60, 61, 62, 63, 64, 65, 66, 67, 68, 70, 71, 73, 74, 75, 78, 79, 80, 81, 82, 83, 86, 87, 89, 90, 91, 92, 93, 95, 96, 97, 98, 99, 100, 101, 102, 103, 104, 105, 106, 108, 109, 110, 111, 112, 113, 114, 115, 116, 120, 121, 122, 123, 125, 126, 128, 129, 130, 131, 132, 133, 134, 136, 137, 139, 146, 158, 166, 170, 171, 191, 243, 248, 258, 269 and 272.

Thus, in an alignment of the Myb41 protein of the present invention to SEQ ID NO. 2 at least the following positions of SEQ ID NO. 2 are preferably preserved: 89, 90, 92, 93, 96, 97, 99, 100, 102, 103, 105, 106, 108, 114 and 170. Furthermore, a Myb41 protein of the present invention preferably comprises the minimal consensus sequence SEQ ID NO. 4. More preferably at least the following positions of SEQ ID NO. 2 are preserved: 15, 17, 21, 22, 25, 28, 29, 33, 37, 40, 44, 45, 46, 48, 50, 51, 52, 53, 54, 55, 56, 57, 59, 60, 61, 62, 63, 64, 74, 78, 81, 82, 86, 87, 89, 90, 92, 93, 96, 97, 99, 100, 101, 102, 103, 104, 105, 106, 108, 109, 114 and 170. Even more preferably at least the following positions of SEQ ID NO. 2 are preserved: 2, 15, 17, 18, 21, 22, 25, 28, 29, 33, 35, 37, 40, 41, 44, 45, 46, 48, 49, 50, 51, 52, 53, 54, 55, 56, 57, 59, 60, 61, 62, 63, 64, 67, 68, 74, 75, 78, 81, 82, 86, 87, 89, 90, 92, 93, 96, 97, 98, 99, 100, 101, 102, 103, 104, 105, 106, 108, 109, 110, 111, 112, 114, 123, 125, 128 and 170. And most preferably at least the following positions of SEQ ID NO. 2 are preserved: 2, 3, 5, 6, 7, 8, 9, 10, 11, 13, 14, 15, 16, 17, 18, 20, 21, 22, 24, 25, 28, 29, 32, 33, 35, 37, 38, 40, 41, 44, 45, 46, 48, 49, 50, 51, 52, 53, 54, 55, 56, 57, 58, 59, 60, 61, 62, 63, 64, 65, 66, 67, 68, 70, 71, 73, 74, 75, 78, 79, 80, 81, 82, 83, 86, 87, 89, 90, 91, 92, 93, 95, 96, 97, 98, 99, 100, 101, 102, 103, 104, 105, 106, 108, 109, 110, 111, 112, 113, 114, 115, 116, 120, 121, 122, 123, 125, 126, 128, 129, 130, 131, 132, 133, 134, 136, 137, 139, 146, 158, 166, 170, 171, 191, 243, 248, 258, 269 and 272.

At those positions where the Myb41 protein of the present invention differs from SEQ ID NO. 2 or 5 in an alignment, that is, where a position, in the numbering according to SEQ ID NO. 2 is not preserved, the difference preferably is in accordance to the amino acids or gaps depicted in FIG. 3 at the respective positions and/or is a phosphomimetic substitution. Thus, preferably any deletion or replacement of amino acids of SEQ ID NO. 2 are chosen according to the amino acids or gaps offered by FIG. 3.

In addition to the selection of amino acids or deletions at the positions indicated above the Myb41 protein may also comprise one insertions. Examples of acceptable insertions are given in FIG. 4. It is preferred that where a Myb41 protein comprises an insertion, the insertion is, in the numbering according to SEQ ID NO. 2, only between those amino acids where according to FIG. 4 an insertion is found. An insertion can be of any length, preferably is of one to 70 amino acids, even more preferably 1 to 50 amino acids and most preferably 1 to 28 amino acids.

In the special case where the Myb41 protein of the present invention comprises a phosphomimetic mutation, this mutation preferably is or comprises, in the numbering according to SEQ ID NO. 2, the substitution S251E or S251D. Corresponding preferred Myb41 amino acid sequences comprising such phosphomimetic substitutions are indicated by SEQ ID NO. 6, 7, 8 or 9. The phosphomimetic mutations render the Myb41 protein of the present invention in a state similar to that of the phosphorylated form of Myb41, thereby obviating the need for a phosphorylation step and increasing the constitutive availability of Myb41 in an activated form. This, in turn, decreases the delay between Myb41 production and onset of fungal resistance.

The following Uniprot entries depict, on the basis of their respective sequences on 5 Nov. 2019, the Myb41 protein of *Arabidopsis thaliana* and homologs thereto: Q9M0J5 (MYB41_ARATH), K7LU39 (K7LU39_SOYBN), A0A445HNS7 (A0A445HNS7_GLYSO), A0A445KFX1 (A0A445KFX1_GLYSO), 11KQR0 (11KQR0_SOYBN), R0GQH1 (R0GQH1_9BRAS), D7MDM8 (D7MDM8_ARALL), V4LUX5 (V4LUX5_EUTSA), A0A0D3A772 (A0A0D3A772_BRAOL), M4EBX2 (M4EBX2_BRARP), A0A398AMS3 (A0A398AMS3_BRACM), A0A078G2Y0 (A0A078G2Y0_BRANA), A0A0D3DG18 (A0A0D3DG18_BRAOL), A0A078JP44 (A0A078JP44_BRANA), A0A397KYM7 (A0A397KYM7_BRACM), A0A3S3NZN7 (A0A3S3NZN7_9MAGN), M4E620 (M4E620_BRARP), A0A078GXG4 (A0A078GXG4_BRANA), A0A1P8B402 (A0A1P8B402_ARATH), A0A2U1Q9L5 (A0A2U1Q9L5_ARTAN), A0A2U1LGR0 (A0A2U1LGR0_ARTAN), A0A3Q7JEJ1 (A0A3Q7JEJ1_SOLLC), A0A3N7G9J4 (A0A3N7G9J4_POPTR) and A0A498JL09 (A0A498JL09_MALDO). Preferably the Myb41 protein of the present invention is any of the aforementioned homologs or differs, when aligned to SEQ ID NO. 2, from the respective homolog's sequence only by the amino acids, gaps or deletions according to FIG. 3 and/or an insertion at a position according to FIG. 4 Even more preferably the Myb41 protein of the present invention is any of the aforementioned homologs or differs, when aligned to SEQ ID NO. 2, from the respective homolog's sequence only by the amino acids, gaps or deletions according to FIG. 3.

Most preferably the Myb41 protein of the present invention comprises of consists of the protein of SEQ ID NO. 2.

The Myb41 gene of the present invention preferably is (i) a nucleic acid sequence having at least 70% identity, at least 80% identity, at least 90% identity, at least 95% identity with SEQ ID NO. 1, or a functional fragment thereof or a splice variant thereof;

(ii) a nucleic acid sequence encoding a protein having at least 70% identity, at least 80% identity, at least 90% identity, at least 95% identity with SEQ ID NO. 2 or 5, or a functional fragment thereof;

(iii) a nucleic acid capable of hybridizing under stringent conditions with a complementary sequence of any of the nucleic acids according to (i) or (ii); or (iv) a nucleic acid encoding the same Myb41 protein as the nucleic acids of (i) to (iii) above, but differing from the nucleic acids of (i) to (iii) above due to the degeneracy of the genetic code.

Protein or nucleic acid variants may be defined by their sequence identity when compared to a parent protein or nucleic acid. Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this invention is that alignment, from which the highest sequence identity can be determined.

The following example is meant to illustrate two nucleotide sequences, but the same calculations apply to protein sequences:

```
Seq A: aagatactg length: 9 bases

Seq B: gatctga length: 7 bases
```

Hence, the shorter sequence is sequence B.

Producing a pairwise global alignment which is showing both sequences over their complete lengths results in

```
Seq A: AAGATACTG-
       ||| |||
Seq B: --GAT-CTGA
```

The "I" symbol in the alignment indicates identical residues (which means bases for DNA or amino acids for proteins). The number of identical residues is 6.

The "-" symbol in the alignment indicates gaps. The number of gaps introduced by alignment within the sequence B is 1. The number of gaps introduced by alignment at borders of sequence B is 2, and at borders of sequence A is 1.

The alignment length showing the aligned sequences over their complete length is 10.

Producing a pairwise alignment which is showing the shorter sequence over its complete length according to the invention consequently results in:

```
Seq A: GATACTG-
       ||| |||
Seq B: GAT-CTGA
```

Producing a pairwise alignment which is showing sequence A over its complete length according to the invention consequently results in:

```
Seq A: AAGATACTG
       ||| |||
Seq B: --GAT-CTG
```

Producing a pairwise alignment which is showing sequence B over its complete length according to the invention consequently results in:

```
Seq A: GATACTG-
       ||| |||
Seq B: GAT-CTGA
```

The alignment length showing the shorter sequence over its complete length is 8 (one gap is present which is factored in the alignment length of the shorter sequence).

Accordingly, the alignment length showing sequence A over its complete length would be 9 (meaning sequence A is the sequence of the invention), the alignment length showing sequence B over its complete length would be 8 (meaning sequence B is the sequence of the invention).

After aligning the two sequences, in a second step, an identity value shall be determined from the alignment. Therefore, according to the present description the following calculation of percent-identity applies:

%–identity=(identical residues/length of the alignment region which is showing the respective sequence of this invention over its complete length)*100. Thus, sequence identity in relation to comparison of two amino acid sequences according to the invention is calculated by dividing the number of identical residues by the length of the alignment region which is showing the respective sequence of this invention over its complete length. This value is multiplied with 100 to give "%–identity". According to the example provided above, %–identity is: for sequence A being the sequence of the invention (6/9)*100=66.7%; for sequence B being the sequence of the invention (6/8) *100=75%.

The term "hybridisation" as defined herein is a process wherein substantially complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point (Tm) for the specific sequence at a defined ionic strength and pH. Medium stringency conditions are when the temperature is 20° C. below Tm, and high stringency conditions are when the temperature is 10° C. below Tm. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore, medium stringency hybridisation conditions may sometimes be needed to identify such nucleic acid molecules.

The "Tm" is the temperature under defined ionic strength and pH, at which 50% of the target sequence hybridises to a perfectly matched probe. The Tm is dependent upon the solution conditions and the base composition and length of the probe. For example, longer sequences hybridise specifically at higher temperatures. The maximum rate of hybridisation is obtained from about 16° C. up to 32° C. below Tm. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

DNA-DNA hybrids (Meinkoth and Wahl, Anal. Biochem., 138: 267-284, 1984): $Tm=81.5°$ C.$+16.6\times$ log($[Na+]\{a\}$)$+0.41\times\%[G/C\{b\}]-500\times[L\{c\}]-1-0.61\times\%$ formamide DNA-RNA or RNA-RNA hybrids: $Tm=79.8+18.5$ (log $10[Na+]\{a\}$)$+0.58$ (% G/C$\{b\}$)$+11.8$ (% G/C$\{b\}$)$2-820/L\{c\}$ oligo-DNA or oligo-RNAd hybrids:

for <20 nucleotides: $Tm=2$ ($\{In\}$)

for 20-35 nucleotides: $Tm=22+1.46$ ($\{In\}$)

wherein:

$\{a\}$ or for other monovalent cation, but only accurate in the 0.01-0.4 M range $\{b\}$ only accurate for % GC in the 30% to 75% range $\{c\}$ L=length of duplex in base pairs $\{d\}$ Oligo, oligonucleotide $\{In\}$ effective length of primer=$2\times$(no. of G/C)+(no. of A/T)

Non-specific binding may be controlled using any one of a number of known techniques such as, for example, blocking the membrane with protein containing solutions, additions of heterologous RNA, DNA, and SDS to the hybridisation buffer, and treatment with Rnase. For non-related probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 µg/ml denatured, fragmented salmon sperm DNA, 0.5% sodium pyrophosphate. Another example of high stringency conditions is hybridisation at 65° C. in 0.1×SSC comprising 0.1 SDS and optionally 5×Denhardt's reagent, 100 µg/ml denatured, fragmented salmon sperm DNA, 0.5% sodium pyrophosphate, followed by the washing at 65° C. in 0.3×SSC.

For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

As used herein, the term "isolated DNA molecule" refers to a DNA molecule at least partially separated from other molecules normally associated with it in its native or natural state. The term "isolated" preferably refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods well known to those skilled in the art can be used to isolate and manipulate a polynucleotide, or fragment thereof, as disclosed herein. For example, polymerase chain reaction (PCR) technology can be used to amplify a particular starting polynucleotide molecule and/or to produce variants of the original molecule. Polynucleotide molecules, or fragment thereof, can also be obtained by other techniques, such as by directly synthesizing the fragment by chemical means, as is commonly practiced by using an automated oligonucleotide synthesizer. A polynucleotide can be single-stranded (ss) or double-stranded (ds). "Double-stranded" refers to the base-pairing that occurs between sufficiently complementary, anti-parallel nucleic acid strands to form a double-stranded nucleic acid structure, generally under physiologically relevant conditions. Embodiments of the method include those wherein the polynucleotide is at least one selected from the group consisting of sense single-stranded DNA (ssDNA), sense single-stranded RNA (ssRNA), double-stranded RNA (dsRNA), double-stranded DNA (dsDNA), a double-stranded DNA/RNA hybrid, anti-sense ssDNA, or anti-sense ssRNA; a mixture of polynucleotides of any of these types can be used.

As used herein, "recombinant" when referring to nucleic acid or polypeptide, indicates that such material has been altered as a result of human application of a recombinant technique, such as by polynucleotide restriction and ligation, by polynucleotide overlap-extension, or by genomic insertion or transformation. A gene sequence open reading frame is recombinant if (a) that nucleotide sequence is present in a context other than its natural one, for example by virtue of being (i) cloned into any type of artificial nucleic acid vector or (ii) moved or copied to another location of the original genome, or if (b) the nucleotide sequence is mutagenized such that it differs from the wild type sequence. The term recombinant also can refer to an organism having a recombinant material, e.g., a plant that comprises a recombinant nucleic acid is a recombinant plant.

The terms "genetically modified" or "transgenic" are used interchangeably herein and refer to an organism, preferably a plant or part thereof, or a nucleic acid that comprises a heterologous polynucleotide. Preferably, the heterologous polynucleotide is stably integrated within the genome such that the polynucleotide is passed on to successive generations. The heterologous polynucleotide may be integrated into the genome alone or as part of a recombinant expression cassette. The heterologous polynucleotide preferably is cisgenic or intragenic. "Transgenic" and "genetically modified" are used herein to refer to any cell, cell line, callus, tissue, plant part or plant, the genotype of which has been so altered by the presence of heterologous nucleic acid including those transgenic organisms or cells initially so altered, as well as those created by crosses or asexual propagation from the initial transgenic organism or cell. A "recombinant" organism preferably is a "transgenic" organism. The term "transgenic" as used herein is not intended to encompass the alteration of the genome (chromosomal or extra-chromosomal) by conventional plant breeding methods (e.g., crosses) or by naturally occurring events such as, e.g., self-fertilization, random cross-fertilization, non-recombinant viral infection, non-recombinant bacterial transformation, non-recombinant transposition, or spontaneous mutation.

As used herein, "mutagenized" refers to an organism or nucleic acid thereof having alteration(s) in the biomolecular sequence of its native genetic material as compared to the sequence of the genetic material of a corresponding wildtype organism or nucleic acid, wherein the alteration(s) in genetic material were induced and/or selected by human action. Examples of human action that can be used to produce a mutagenized organism or DNA include, but are not limited to treatment with a chemical mutagen such as EMS and subsequent selection with herbicide(s); or by treatment of plant cells with x-rays and subsequent selection with herbicide(s). Any method known in the art can be used to induce mutations. Methods of inducing mutations can induce mutations in random positions in the genetic material or can induce mutations in specific locations in the genetic material (i.e., can be directed mutagenesis techniques), such as by use of a genoplasty technique. In addition to unspecific mutations, according to the invention a nucleic acid can also be mutagenized by using mutagenesis means with a preference or even specificity for a particular site, thereby creating an artificially induced heritable allele according to the present invention. Such means, for example site specific nucleases, including for example zinc finger nucleases (ZFNs), meganucleases, transcription activator-like effector nucleases (TALENS) (Malzahn et al., Cell Biosci, 2017, 7:21) and clustered regularly interspaced short palindromic repeats/CRISPR-associated nuclease (CRISPR/Cas) with an engineered crRNA/tracr RNA (for example as a single-guide RNA, or as modified crRNA and tracrRNA molecules which form a dual molecule guide), and methods of using this nucleases to target known genomic locations, are well-known in the art (see reviews by Bortesi and Fischer, 2015, Biotechnology Advances 33: 41-52; and by Chen and Gao, 2014, Plant Cell Rep 33: 575-583, and references within).

As used herein, a "genetically modified organism" (GMO) is an organism whose genetic characteristics contain alteration(s) that were produced by human effort causing transfection that results in transformation of a target organism with genetic material from another or "source" organism, or with synthetic or modified-native genetic material, or an organism that is a descendant thereof that retains the inserted genetic material. The source organism can be of a different type of organism (e.g., a GMO plant can contain bacterial genetic material) or from the same type of organism (e.g., a GMO plant can contain genetic material from another plant).

As used herein, "wildtype" or "corresponding wildtype plant" means the typical form of an organism or its genetic material, as it normally occurs, as distinguished from e.g. mutagenized and/or recombinant forms. Similarly, by "control cell" or "similar, wildtype, plant, plant tissue, plant cell or host cell" is intended a plant, plant tissue, plant cell, or host cell, respectively, that lacks the particular polynucleotide of the invention that are disclosed herein. The use of the term "wildtype" is not, therefore, intended to imply that a plant, plant tissue, plant cell, or other host cell lacks recombinant DNA in its genome, and/or does not possess fungal resistance characteristics that are different from those disclosed herein.

As used herein, "descendant" refers to any generation plant. A progeny or decendant plant can be from any filial generation, e.g., F1, F2, F3, F4, F5, F6, F7, etc. In some embodiments, a descendant or progeny plant is a first, second, third, fourth, fifth, sixth, seventh, eighth, ninth, or tenth generation plant.

The term "plant" is used herein in its broadest sense as it pertains to organic material and is intended to encompass eukaryotic organisms that are members of the taxonomic kingdom plantae, examples of which include but are not limited to monocotyledon and dicotyledon plants, vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). Unless stated otherwise, the term "plant" refers to a whole plant, any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant.

The invention in particular pertains to plants in general and preferably to crop plants, that is plants selected from the group consisting of members of the taxonomic family Fabaceae, Brassicaceae and Poaceae, most preferably soy. More preferably, the crop plant is selected from the group consisting of taxonomic *tribus* Phaseoleae, more preferably of genus *Cajanus, Canavalia, Glycine, Phaseolus, Psophocarpus, Pueraria* or *Vigna*, even more preferably of species *Cajanus cajan, Canavalia brasiliensis, Canavalia ensiformis, Canavalia gladiata, Glycine gracilis, Glycine max, Glycine soja, Phaseolus acutifolius, Phaseolus lunatus, Phaseolus maculatus, Psophocarpus tetragonolobus, Pueraria montana, Vigna angularis, Vigna mungo, Vigna radiata* or *Vigna unguiculata*, even more preferably of species *Glycine gracilis, Glycine max* or *Glycine soja*, even more preferably of species *Glycine max*; or of taxonomic *tribus* Fabeae, more preferably of genus *Lathyrus, Lens, Pisum* or *Vicia*, even more preferably of species *Lathyrus aphaca, Lathyrus cicera, Lathyrus hirsutus, Lathyrus ochrus, Lathyrus odoratus, Lathyrus sphaericus, Lathyrus tingitanus, Lens culinaris, Pisum sativum, Vicia cracca, Vicia faba* or *Vicia vellosa*; or of taxonomic *tribus* Brassiceae, more preferably of genus *Brassica, Crambe, Raphanus* or *Sinapis*, even more preferably of species *Brassica aucheri, Brassica balearica, Brassica barrelieri, Brassica bourgeaui, Brassica carinata, Brassica cretica, Brassica deflexa, Brassica desnottesii, Brassica drepanensis, Brassica elongata, Brassica fruticulosa, Brassica gravinae, Brassica hilarionis, Brassica incana, Brassica insularis, Brassica juncea, Brassica macrocarpa, Brassica maurorum, Brassica montana, Brassica napus, Brassica nigra, Brassica oleracea, Brassica oxyrrhina, Brassica procumbens, Brassica rapa, Brassica repanda, Brassica rupestris, Brassica souliei, Brassica spinescens, Brassica toumefortii, Brassica villosa* or crosses of any of these species, even more preferably *Brassica napus* (rape), *Brassica nigra* (black mustard), *Brassica oleracea* (wild cabbage), *Brassica rapa* (field mustard) or crosses of any of these species, even more preferably *Brassica napus,* species *Raphanus sativus,* species *Sinapis alba*; or of taxonomic *tribus* Andropogoneae, Bambuseae, Oryzeae, Poeae, Triticeae, more preferably of genus *Saccharum, Zea, Oryza, Avena, Hordeum, Secale, Triticum,* even more preferably of species *Zea mays, Oryza sativa, Avena sativa, Avena strigosa, Hordeum marinum, Hordeum vulgare, Secale cereale* or *Triticum aestivum,* and preferably the plant is soy.

The term "seed" comprises seeds of all types, such as, for example, true seeds, caryopses, achenes, fruits, tubers, seedlings and similar forms. Preferably "seed" refers to true seed(s) unless otherwise specified. For example, the seed can be seed of transgenic plants or plants obtained by site specific mutagenesis, by mutagenesis with a site preference or by traditional breeding methods. Examples of traditional breeding methods are cross-breeding, selfing, back-crossing, embryo rescue, in-crossing, out-crossing, inbreeding, selection, asexual propagation, and other traditional techniques as are known in the art.

The present invention is particularly useful for fighting against a plant pathogenic fungus. According to the invention the fungus to fight against is preferably a biotrophic, hemibiotrophic or heminecrotrophic fungus, more preferably a rust fungus, downy mildew, powdery mildew, leaf spot, late blight, *fusarium* and/or *Septoria*, and is even more preferably selected from the taxonomic phylum Basidiomycota, more preferably the taxonomic class Pucciniomycetes, more preferably the taxonomic class Pucciniales, more preferably the taxonomic family Pucciniaceae, more preferably the taxonomic genus *Puccinia*, more preferably the taxonomic species *Puccinia graminis*; or phylum Basidiomycota, more preferably the taxonomic class Pucciniomycetes, more preferably the taxonomic order Pucciniales, more preferably the taxonomic family Phakopsoraceae, more preferably the taxonomic genus *Phakopsora*, more preferably the taxonomic species *Phakopsora pachyrhizi* or *Phakopsora meibomiae*; or phylum Ascomycota, more preferably the taxonomic class Sordariomycetes, more preferably the taxonomic order Hypocreales, more preferably the taxonomic family Nectriaceae, more preferably the taxonomic genus *Fusarium*, more preferably the taxonomic species *Fusarium graminearum* or *Fusarium verticillioides.*

It is a particularly preferable advantage that the materials and methods of the present invention are useful for fighting against rust fungi of genus *Phakopsora*, in particular and most preferred *Phakopsora pachyrhizi*. These fungal pathogens are responsible for huge losses of soybean when soybean plants are left untreated. The present invention thus allows to reduce the number of fungicide treatments by reducing the fungal pathogen pressure.

The present invention in particular provides materials, preferably plants, plant parts or plant cells, or methods to increase fungal resistance. According to the invention, increase of fungal resistance is achieved preferably by reducing, compared to a corresponding wild type, the speed of infection or the extent of infection or delaying the day of earliest infection by the fungus. Thus, the Myb41 protein and gene of the present invention is suitable for conferring, intensifying or stabilising resistance of plants, plant parts or plant cells against fungal pathogen infections, particularly against biotrophic, hemibiotrophic or heminecrotrophic fungi, and preferably against fungi as described herein. Furthermore, by increasing fungal resistance as described in this paragraph the Myb41 protein and gene of the present invention are suitable to prevent, reduce or delay the spread of fungal spores to other fields, thereby also reducing pathogen pressure in the wider area where the plants expressing the Myb41 protein of the present invention are grown. And, by increasing fungal resistance as described in this paragraph the Myb41 protein and gene of the present invention are suitable to reduce the number of fungicide treatments required to protect growing plants.

The invention correspondingly provides a method for conferring or increasing fungal resistance in a plant, a plant part, or a plant cell wherein the method comprises the step of increasing the production and/or accumulation of Myb41 in the plant, plant part, or plant cell in comparison to a respective wild type plant, wild type plant part, or wild type plant cell. As described above it was surprising that a gene known only for its role in management of osmotic stress could have the beneficial effect of increasing fungal resistance in particular in species other than *Arabidopsis.*

The invention also provides a method of conferring or increasing fungal resistance in a plant, a plant part, or a plant cell, wherein the method comprises increasing the expression and/or biological activity of a Myb41 protein in the plant, plant part, or plant cell in comparison to a respective wild type plant, wild type plant part, or wild type plant cell, wherein said Myb41 protein is encoded by (i) an exogenous nucleic acid having at least 70% identity, at least 80% identity, at least 90% identity, at least 95% identity with SEQ ID NO. 1, or a functional fragment thereof or a splice variant thereof;

(ii) an exogenous nucleic acid encoding a protein having at least 70% identity, at least 80% identity, at least 90% identity, at least 95% identity with SEQ ID NO. 2 or 5, or a functional fragment thereof;

(iii) an exogenous nucleic acid capable of hybridizing under stringent conditions with a complementary sequence of any of the nucleic acids according to (i) or (ii); or (iv) an exogenous nucleic acid encoding the same Myb41 protein as the nucleic acids of (i) to (iii) above, but differing from the nucleic acids of (i) to (iii) above due to the degeneracy of the genetic code. Again, the method surprisingly and beneficially increases fungal resistance as described herein.

Preferably the method comprises the steps of (a) stably transforming a plant cell with at least one expression cassette comprising an exogenous nucleic acid encoding a Myb41 protein, (b) regenerating a plant from the plant cell; and (c) expressing said Myb41 protein. Expression of the Myb41 protein of the present invention surprisingly confers or increases fungal resistance of the plant as described herein.

Preferably the aforementioned methods of the present invention comprises the step of phosporylating the Myb41 protein in the respective plant, plant part, or plant cell, preferably at the serin at position 251 of SEQ ID NO. 2. Without being bound by any specific theory it is expected that phosphorylation increases the availability of functional Myb41 protein to plant cells. Correspondingly, phosphomimetic forms of the Myb41 protein of the present invention are described above, in particular with reference to SEQ ID NO. 6, 7, 8 or 9.

The term "functional" means that the respective plant, plant part or plant cell is more likely to withstand an attempted infection by the pathogenic fungus, preferably *Phakopsora pachyrhizi*.

The invention also provides a recombinant vector construct comprising a nucleic acid encoding a Myb41 protein selected from the group consisting of:

(i) a nucleic acid having at least 70% identity, at least 80% identity, at least 90% identity, at least 95% identity with SEQ ID NO. 1 or a functional fragment thereof, or a splice variant thereof;

(ii) a nucleic acid coding for a protein having at least 70% identity, at least 80% identity, at least 90% identity, at least 95% identity with SEQ ID NO. 2 or 5 or a functional fragment thereof;

(iii) an exogenous nucleic acid capable of hybridizing under stringent conditions with a complementary sequence of any of the nucleic acids according to (i) or (ii); or (iv) a nucleic acid encoding the same Myb41 protein as the nucleic acids of (i) to (iii) above, but differing from the nucleic acids of (i) to (iii) above due to the degeneracy of the genetic code;

operably linked to a promoter and a transcription termination sequence, and wherein the nucleic acid does not encode a protein of the amino acid sequence SEQ ID NO. 2. Such vectors are particularly useful for transforming plants to express a Myb41 gene of the present invention to confer or increase fungal resistance in a plant, plant part or plant cell.

The promoter preferably is a constitutive, pathogen-inducible promoter, a mesophyll-specific promoter or an epidermis specific-promoter. The selection of any of these promoters allows to produce, in a plant cell, a respectively constitutively increased level of Myb41 protein, or an increased level in response to a pathogen infection, preferably a fungal pathogen, or to increase the level of Myb41 specifically in mesophyll or plant epidermis cells.

Correspondingly the invention provides a transgenic plant, transgenic plant part, or transgenic plant cell transformed with one or more recombinant vector construct(s) as described according to the invention.

And it is of particular benefit for fungal resistance that the invention provides a crop plant, crop plant part or crop plant cell overexpressing a Myb41 protein, wherein said Myb41 protein is encoded by (i) a nucleic acid having at least 70% identity, at least 80% identity, at least 90% identity, at least 95% identity with SEQ ID NO. 1 or a functional fragment thereof, or a splice variant thereof;

(ii) a nucleic acid coding for a protein having at least 70% identity, at least 80% identity, at least 90% identity, at least 95% identity with SEQ ID NO. 2 or 5 or a functional fragment thereof;

(iii) an exogenous nucleic acid capable of hybridizing under stringent conditions with a complementary sequence of any of the nucleic acids according to (i) or (ii); or (iv) a nucleic acid encoding the same Myb41 protein as the nucleic acids of (i) to (iii) above, but differing from the nucleic acids of (i) to (iii) above due to the degeneracy of the genetic code;

wherein the nucleic acid according to any of (i)-(iv) is operably linked with a promoter and a transcription termination sequence, and preferably wherein (a) the crop plant, crop plant part or crop plant cell is a transgenic crop plant, crop plant part or crop plant cell, or the overexpression results form an artificially induced heritable mutation of the wild type genome; and/or (b) wherein the gene encoding Myb41 is integral in the genome of the plant, plant part or plant cell and/or (c) wherein the plant or plant part is homozygous for the gene encoding Myb41 or heterozygous for the gene encoding Myb41, and/or (d) wherein the plant or plant part, when in meiosis, is non-segregating or segregating for the gene encoding Myb41, and/or (e) wherein the gene encoding Myb41 is operably linked to a heterologous promoter, and/or (f) wherein the gene encoding Myb41 is, in the genome of the plant or plant part, integrated at a different locus than the corresponding wild type Myb41 gene.

The CRISPR (clustered regularly interspaced short palindromic repeats) technology may be used to modify the genome of a target organism, for example to introduce any given DNA fragment into nearly any site of the genome, to replace parts of the genome with desired sequences or to precisely delete a given region in the genome of a target organism. This allows for unprecedented precision of genome manipulation.

The CRISPR system was initially identified as an adaptive defense mechanisms of bacteria belonging to the genus of *Streptococcus* (WO2007/025097). Those bacterial CRISPR systems rely on guide RNA (gRNA) in complex with cleaving proteins to direct degradation of complementary sequences present within invading viral DNA. The application of CRISPR systems for genetic manipulation in various eukaryotic organisms have been shown (WO20131141680; WO2013/176772; WO2014/093595). Cas9, the first identified protein of the CRISPR/Cas system, is a large monomeric DNA nuclease guided to a DNA target sequence adjacent to the PAM (protospacer adjacent motif) sequence motif by a complex of two noncoding RNAs: CRSIPR RNA (crRNA) and trans-activating crRNA (tracrRNA). Also a synthetic RNA chimera (single guide RNA or sgRNA) created by fusing crRNA with tracrRNA was shown to be equally functional (WO2013/176772). CRISPR systems from other sources comprising DNA nucleases distinct from Cas9 such as Cpf1, C2c1p or C2c3p have been described having the same functionality (WO2016/0205711, WO2016/205749). Other authors describe systems in which the nuclease is guided by a DNA molecule instead of an RNA molecule. Such system is for example the AGO system as disclosed in US2016/0046963.

Several research groups have found that the CRISPR cutting properties could be used to disrupt target regions in almost any organism's genome with unprecedented ease. Recently it became clear that providing a template for repair allows for editing the genome with nearly any desired sequence at nearly any site, transforming CRISPR into a powerful gene editing tool (WO2014/150624, WO2014/204728). The template for repair is addressed as donor nucleic acid comprising at the 3' and 5' end sequences complementary to the target region allowing for homologous recombination in the respective template after introduction of doublestrand breaks in the target nucleic acid by the respective nuclease.

The main limitation in choosing the target region in a given genome is the necessity of the presence of a PAM sequence motif close to the region where the CRISPR related nuclease introduces doublestrand breaks. However, various CRISPR systems recognize different PAM sequence motifs. This allows choosing the most suitable CRISPR system for a respective target region. Moreover, the AGO system does not require a PAM sequence motif at all.

The technology may for example be applied for alteration of gene expression in any organism, for example by exchanging the promoter upstream of a target gene with a promoter of different strength or specificity. Other methods disclosed in the prior art describe the fusion of activating or repressing transcription factors to a nuclease minus CRISPR nuclease protein. Such fusion proteins may be expressed in a target organism together with one or more guide nucleic acids guiding the transcription factor moiety of the fusion protein to any desired promoter in the target organism (WO2014/099744; WO2014/099750). Knockouts of genes may easily be achieved by introducing point mutations or deletions into the respective target gene, for example by inducing non-homologous-end-joining (NHEJ) which usually leads to gene disruption (WO2013/176772).

Thus, the invention also provides an ensemble of at least 50 crop plants according to the present invention, more preferably at least 100 plants, even more preferably at least 1000 plants, even more preferably at least 100000 plants. According to the invention, preferably at least 100000 plants are grown per hectar, more preferably 200000 to 800000 plants per hectar, even more preferably at least 250000 to 650000 plants per hectar. Such plant numbers preferably are observed within one hectar; thus, the invention particularly facilitates ecologically considerate intensive farming with reduced use of fungicides per growing season. The plants according to the invention are preferably growing in a field or greenhouse. Preferably the crop plants are soy plants.

According to the invention it is not required that all crop plants of one species growing in the same field or greenhouse are plants of the present invention. Instead, it is sufficient in monoculture plantation if at least about 25% of the plants of one species belong to the present invention, more preferably at least 50%, even more preferably 25%-75% and most preferably 45%-70%, especially when mixed or combined with plants harboring other resistance genes or mechanisms. The combination with plants with other resistance gene can be done by interplanting (mixing), row-wise or blockwise. For example, on a soybean field it is possible to reduce the number of fungicide treatments if approximately every second plant is a plant according to the present invention. It is particularly preferred that at least 25%, more preferably 50%-100% and even more preferably 75%-100% of those plants on the same field that are not plants according to the present invention comprise at least one other biological means for enhancing fungal resistance, most preferably the other means is selected from the list of pathogen resistance polypeptides as described above.

The invention also provides a method for the production of a transgenic crop plant, transgenic crop plant part, or transgenic crop plant cell having increased fungal resistance compared to a respective wild type plant, plant part or plant cell, comprising (a) introducing an exogenous nucleic acid encoding a Myb41 protein into a plant, a plant part, or a plant cell, (b) generating a transgenic plant, transgenic plant part, or transgenic plant cell from the plant, plant part or plant cell; and (c) expressing the Myb41 protein in the transgenic plant, transgenic plant part, or transgenic plant cell from the plant, wherein said Myb41 protein is encoded by (i) a nucleic acid having at least 70% identity, at least 80% identity, at least 90% identity, at least 95% identity with SEQ ID NO. 1 or a functional fragment thereof, or a splice variant thereof;

(ii) a nucleic acid coding for a protein having at least 70% identity, at least 80% identity, at least 90% identity, at least 95% identity with SEQ ID NO. 2 or 5 or a functional fragment thereof;

(iii) an exogenous nucleic acid capable of hybridizing under stringent conditions with a complementary sequence of any of the nucleic acids according to (i) or (ii); or (iv) a nucleic acid encoding the same Myb41 protein as the nucleic acids of (i) to (iii) above, but differing from the nucleic acids of (i) to (iii) above due to the degeneracy of the genetic code operably linked with a promoter and a transcription termination sequence. As described above such method is particularly suitable for conferring or increasing fungal resistance in a plant, plant part or plant cell.

The invention also provides a method of assaying a plant for resistance to a fungus, comprising the screening for the overexpression of a Myb41 gene in a cell of said plant. As described herein, overexpression of Myb41 increases resistance, particularly of crop plants, against fungal infections, particularly by *Phakopsora pachyrhizi*. It is useful to prepare the plants to be screened in the absence of osmotic stress to prevent an unwarranted accidental increase in Myb41 expression levels.

The invention also provides a method for breeding a fungal resistant crop plant comprising (a) crossing the plant of the present invention or the plant obtainable by the method of the present invention with a second plant;

(b) obtaining seed from the cross of step (a);

(c) planting said seeds and growing the seeds to plants; and (d) selecting from said plants plants expressing Myb41 protein as defined above. This method beneficially allows to confer the trait of increased fungal resistance achieved according to the present invention to plants other than by transformation or other direct interference, for example by CRISPR-mediated methods. Thus, the breeding methods beneficially allows for a high speed of plant propagation.

Further advantages and beneficial effects of the present invention are described in the examples and figures appended hereto.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The sequence of the cDNAs of the Myb41 gene mentioned in this application were generated by DNA synthesis (Geneart, Thermo Fisher Scientific, Waltham, Massachusetts, USA).

The Myb41 cDNA (as shown in SEQ ID NO. 1) was synthesized in a way that an Ascl restriction site is located in front of the start-ATG and a Sbfl restriction site downstream of the stop-codon. The synthesized DNA was digested using the restriction enzymes Sbfl and Ascl (NEB Biolabs) and ligated in a Sbfl/Ascl digested binary plant transformation vector in a way that the full-length fragment is located in sense direction between the parsley ubiquitin promoter and the *Agrobacterium tumefaciens* derived nopaline synthase terminator (t-nos). The PcUbi promoter regulates constitutive expression of the ubi4-2 gene (EMBL accession number X64345) of Petroselinum crispum (Kawalleck et al. 1993 Plant Molecular Biology 21(4): 673-684).

The binary plant transformation vector used in this applications was composed of: (1) a Kanamycin resistance cassette for bacterial selection (2) a pVS1 origin for replication in Agrobacteria (3) a ColE1 origin of replication for stable maintenance in *E. coli* and (4) between the right and left border an double mutated AHAS (Acetohydroxyacid synthase Large-SubUnit) selection marker derived from *Arabidopsis thaliana* under control of it native promoter (p-AtAHASL5'; see FIG. 2). The ligation reaction was transformed into *E. coli* (DH5alpha), mini-prepped and screened by specific restriction digestions. A positive clone was sequenced and submitted soy transformation.

Example 3: Soy Transformation

The expression vector constructs (see example 2) were transformed into soy.

3.1 Sterilization and Germination of Soy Seeds

Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 μM 6-benzyl-aminopurine (BAP) in 100 mm Petri dishes. Seedlings without BAP are more elongated and roots develop especially secondary and lateral root formation. BAP strengthens the seedling by forming a shorter and stockier seedling.

Seven-day-old seedlings grown in the light (>100 pEin-stein/$m^2$s) at 25 degree C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3. and 3.3.2) or leaf explants see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium YEP media: 10 g yeast extract. 10 g Bacto Peptone. 5 g NaCl. Adjust pH to 7.0, and bring final volume to 1 liter with H2O, for YEP agar plates add 20 g Agar, autoclave) and incubating at 25.degree C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 μl to 3 ml of working *Agrobacterium* stock in a 500 ml Erlenmeyer flask. The flask was shaken overnight at 25° C. until the $OD_{600}$ was between 0.8 and 1.0. Before preparing the soy explants, the Agrobacteria were pelleted by centrifugation for 10 min at 5,500×g at 20° C.

The pellet was resuspended in liquid CCM to the desired density ($OD_{600}$=0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel. This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in ⅒ MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soybean plants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess *Agrobacterium*) (SIM, see Olhoft et al 2007 A novel *Agrobacterium rhizogenes*-mediated transformation method of soy using primary-node explants from seedlings In Vitro Cell. Dev. Biol.-Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 µE/m²s. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).
3.5—Shoot Elongation After 2 to 4 weeks (or until a mass of shoots was formed) on SIM medium (preferably with selection), the explants were transferred to SEM medium (shoot elongation medium, see Olhoft et al., a novel *Agrobacterium rhizogenes*-mediated transformation method of soy using primary-node explants from seedlings. In Vitro Cell. Dev. Biol.-Plant (2007) 43:536-549) that stimulates shoot elongation of the shoot primordia. This medium may or may not contain a selection compound.

After every 2 to 3 weeks, the explants were transfer to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soybean genome. In addition, preliminary experiments resulted in the formation of cDNA expressing shoots forming after 3 weeks on SIM.

For Method C, the average regeneration time of a soybean plantlet using the propagated axillary meristem protocol was 14 weeks from explant inoculation. Therefore, this method has a quick regeneration time that leads to fertile, healthy soybean plants.

Example 4: Pathogen Assay 4.1. Growth of Plants
10 T1 plants per event were potted and gown for 3-4 weeks in the phytochamber (16 h-day-und 8 h-night-Rhythm at a temperature of 16° and 22° C. und a humidity of 75%) till the first 2 trifoliate leaves were fully expanded.
4.2 Inoculation
The plants were inoculated with spores of *P. pachyrhizi*. In order to obtain appropriate spore material for the inoculation, soybean leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of $1-5\times10^5$ spores/ml. For the microscopy, a density of $>5\times10^5$ spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

Figure 1:
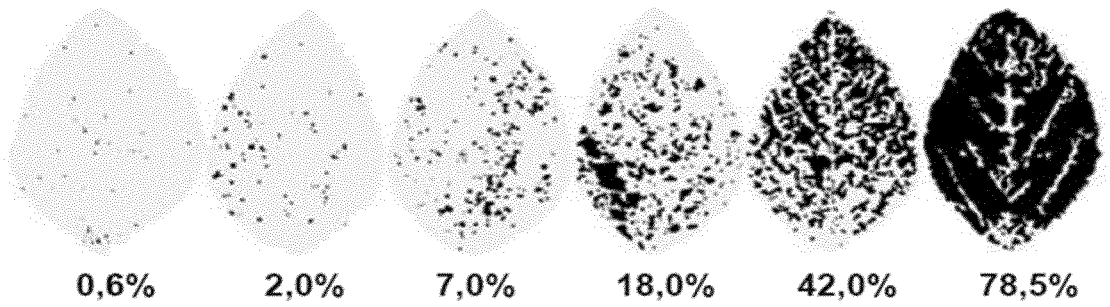
FIG. 1 shows the scoring system used to determine the level of diseased leaf area of wildtype and transgenic soy plants against the rust fungus *P. pachyrhizi* (as described in GODOY, C. V., KOGA, L. J. & CANTERI, M. G. Diagram-

The progression of the soybean rust disease was scored 14 days after inoculation (see example 4) by the estimation of the diseased area (area which was covered by sporulating uredinia) on the adaxial leaf side. Additionally, the yellowing of the leaf was taken into account. (for scheme see FIG. 1).

At all 107 T1 soybean plants, representing 9 independent transformation events (11-12 plants per event) and expressing Myb41 protein were inoculated with spores of *Phakopsora pachyrhizi* (see example 4). The macroscopic disease symptoms of soybean after infection with *P. pachyrhizi* were scored 14 days after inoculation. Plants were grown and kept under the conditions described in example 4.

The average of the percentage of the leaf area showing fungal colonies or strong yellowing/browning was considered as diseased leaf area. All 107 transgenic T1 soybean plants expressing Myb41 (expression checked by RT-PCR) were grown and evaluated in parallel to non-transgenic control plants with the same genetic background as used for the transformation (see example 3).

The average of the diseased leaf area for plants expressing recombinant Myb41 protein and respective wildtype control plants is shown in FIG. 5. Both, transgenic T1 soybean plants expressing Myb41 and non-transgenic wild type control plants are based on the same genetic background.

Overexpression of the Myb41 protein reduces the diseased leaf area in comparison to non-transgenic control plants by 33.5% in average over all events and plants generated. This difference is statistically significant on a $p < 0.001$ level (two-sided student's t-test). The data clearly shows that the in-planta expression of the Myb41 expression vector construct (see FIG. 2) leads to a lower disease in transgenic plants compared to wild type controls. So, the expression of Myb41 protein (as shown in SEQ ID NO. 2) in soybean increases the resistance of soy against soybean rust.

The invention claimed is:

1. A method for reducing or delaying *Phakopsora* infection in a soybean plant, a soybean plant part, or a soybean plant cell, the method comprising:

(1) providing a transgenic soybean plant, transgenic soybean plant part, or transgenic soybean plant cell with an exogenous nucleic acid encoding a Myb41 protein having an amino acid sequence with at least 90% identity with SEQ ID NO. 2 or 5, wherein expression of the Myb41 protein confers increased resistance against *Phakopsora* thereto in comparison to a wild type soybean plant, wild type soybean plant part or wild type soybean plant cell; and (2) growing the transgenic soybean plant, transgenic soybean plant part, or transgenic soybean plant cell in the presence of a fungal pathogen of the genus *Phakopsora*, wherein *Phakopsora* infection is reduced or delayed in the transgenic soybean plant, transgenic soybean plant part, or transgenic soybean plant cell as compared to a wild type soybean plant, wild type soybean plant part, or wild type soybean plant cell.

2. The method according to claim 1, further comprising the step of phosphorylating the Myb41 protein in the respective plant, plant part, or plant cell.

3. The method according to claim 1, wherein the Myb41 protein comprises a phosphomimetic mutation.

4. The method according to claim 1, wherein the Myb41 protein has an amino acid sequence with at least 95% identity to SEQ ID NO. 2 or 5.

\* \* \* \* \*

SEQUENCE LISTING

```
<160> NUMBER OF SEQ ID NOS: 42

<210> SEQ ID NO 1
<211> LENGTH: 849
<212> TYPE: DNA
<213> ORGANISM: Artificial Sequence
<220> FEATURE:
<223> OTHER INFORMATION: Synthetic polynucleotide coding for Myb41
      protein SEQ ID NO: 2

<400> SEQUENCE: 1
atgggaagat caccttgttg tgataaaaat ggagtgaaga agggaccatg gactgctgag          60
gaggatcaga aactcatcga ttatattcga tttcatggtc ctggcaattg gcgtacgctc         120
cccaaaaatg ctggactcca tagatgtgga aaaagctgcc gtcttcgatg gaccaattat         180
ctaagaccgg acatcaagag aggaagattc tcgttcgagg aagaagaaac tatcattcag         240
ctacacagtg ttatgggaaa caagtggtca gcaatagccg ctcgtctacc agggaggacc         300
gataacgaaa taaaaaacca ttggaacact cacatccgca agagacttgt aaggagtggt         360
atcgaccctg ttactcattc tccacgcctt gatcttcttg atttgtcctc acttttgagt         420
gcacttttca accagccaaa cttttcagca gttgcaacac atgcgtcttc tcttcttaat         480
cctgatgtat tgaggttggc ctctctacta ctgccacttc aaaaccctaa tccagtttac         540
ccatcgaacc tcgaccaaaa tcttcaaact ccaaatacat catcagaatc gtctcaacca         600
caagctgaga ctagtacagt cccaacaaac tatgaaactt catcattgga gcctatgaac         660
gcaagactcg acgacgttgg tcttgcagat gtattaccac ctttgtcaga gagttttgac         720
ttagactcgc tcatgtcaac gccaatgtct tctccacgac aaaatagcat tgaagcagaa         780
accaactcca gcactttctt cgactttgga attccggaag atttcatctt agatgacttt         840
atgttttaa                                                                  849

<210> SEQ ID NO 2
<211> LENGTH: 282
<212> TYPE: PRT
<213> ORGANISM: Arabidopsis thaliana

<400> SEQUENCE: 2

Met Gly Arg Ser Pro Cys Cys Asp Lys Asn Gly Val Lys Lys Gly Pro
1               5                   10                  15

Trp Thr Ala Glu Glu Asp Gln Lys Leu Ile Asp Tyr Ile Arg Phe His
            20                  25                  30
```

-continued

```
Gly Pro Gly Asn Trp Arg Thr Leu Pro Lys Asn Ala Gly Leu His Arg
        35                  40                  45

Cys Gly Lys Ser Cys Arg Leu Arg Trp Thr Asn Tyr Leu Arg Pro Asp
    50                  55                  60

Ile Lys Arg Gly Arg Phe Ser Phe Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
            115                 120                 125

Arg Leu Asp Leu Leu Asp Leu Ser Ser Leu Leu Ser Ala Leu Phe Asn
    130                 135                 140

Gln Pro Asn Phe Ser Ala Val Ala Thr His Ala Ser Ser Leu Leu Asn
145                 150                 155                 160

Pro Asp Val Leu Arg Leu Ala Ser Leu Leu Leu Pro Leu Gln Asn Pro
                165                 170                 175

Asn Pro Val Tyr Pro Ser Asn Leu Asp Gln Asn Leu Gln Thr Pro Asn
            180                 185                 190

Thr Ser Ser Glu Ser Ser Gln Pro Gln Ala Glu Thr Ser Thr Val Pro
            195                 200                 205

Thr Asn Tyr Glu Thr Ser Ser Leu Glu Pro Met Asn Ala Arg Leu Asp
    210                 215                 220

Asp Val Gly Leu Ala Asp Val Leu Pro Pro Leu Ser Glu Ser Phe Asp
225                 230                 235                 240

Leu Asp Ser Leu Met Ser Thr Pro Met Ser Ser Pro Arg Gln Asn Ser
                245                 250                 255

Ile Glu Ala Glu Thr Asn Ser Ser Thr Phe Phe Asp Phe Gly Ile Pro
            260                 265                 270

Glu Asp Phe Ile Leu Asp Asp Phe Met Phe
            275                 280
```

```
<210> SEQ ID NO 3
<211> LENGTH: 1497
<212> TYPE: DNA
<213> ORGANISM: Arabidopsis thaliana

<400> SEQUENCE: 3
tacatccaca cattgacatt tctaaaatcc aactcctctt tttgaaaatt aagaaactcc      60
acttggctct tcgatttttt ctatctaaat aacagaacca aatcattatc gaaatttaaa     120
gttgtgcgaa acaaaacaaa gatgggaaga tcaccttgtt gtgataaaaa tggagtgaag     180
aagggaccat ggactgctga ggaggatcag aaactcatcg attatattcg atttcatggt     240
cctggcaatt ggcgtacgct ccccaaaaat gctggtacgt ataaactaca caccgttcct     300
tatattttgt tctcatagat taatatatat gttctctatt tattgagtca cacacttata     360
agtcgtattg tacaaattaa aggactccat agatgtggaa aaagctgccg tcttcgatgg     420
accaattatc taagaccgga catcaagaga ggaagattct cgttcgagga agaagaaact     480
atcattcagc tacacagtgt tatgggaaac aagtaagcct gatcattcac accataattt     540
ttgtctgaaa ttcatattca tcagctacat gcttttgtat gttaattaat gtaaaactca     600 aaaaggggaga gtgtacgttt gcatgcgggg gtacatgtca aatgtaggcc atcaactcca     660
ataaactatt attagtactt tactagtacg tattgaccta tattagaata ataataaagg     720
```

-continued

```
agttttgtat tgatcataga ttaatgtcac taatattgaa ttgatgaata ttaggtggtc    780
agcaatagcc gctcgtctac cagggaggac cgataacgaa ataaaaaacc attggaacac    840
tcacatccgc aagagacttg taaggagtgg tatcgaccct gttactcatt ctccacgcct    900
tgatcttctt gatttgtcct cacttttgag tgcacttttc aaccagccaa acttttcagc    960
agttgcaaca catgcgtctt ctcttcttaa tcctgatgta ttgaggttgg cctctctact   1020
actgccactt caaaacccta atccagttta cccatcgaac ctcgaccaaa tcttcaaac    1080 tccaaataca tcatcagaat cgtctcaacc acaagctgag actagtacag tcccaacaaa   1140
ctatgaaact tcatcattgg agcctatgaa cgcaagactc gacgacgttg gtcttgcaga   1200
tgtattacca cctttgtcag agagttttga cttagactcg ctcatgtcaa cgccaatgtc   1260
ttctccacga caaaatagca ttgaagcaga aaccaactcc agcactttct tcgactttgg   1320
aattccggaa gatttcatct tagatgactt tatgttttaa ttttcaacat ttgcatacac   1380
atgtcttgct ttcacacata tgattctttg ttgcattctt tctttgttt gatgtataaa    1440 tttcttgttt ttattctctc aaaagatatt aagttattag tctataaaat tttcatg      1497
```

```
<210> SEQ ID NO 4
<211> LENGTH: 20
<212> TYPE: PRT
<213> ORGANISM: Artificial Sequence
<220> FEATURE:
<223> OTHER INFORMATION: Minimal consensus sequence
<220> FEATURE:
<221> NAME/KEY: MISC_FEATURE
<222> LOCATION: (3)..(3)
<223> OTHER INFORMATION: Xaa can be any proteinogenic amino acid
<220> FEATURE:
<221> NAME/KEY: MISC_FEATURE
<222> LOCATION: (6)..(7)
<223> OTHER INFORMATION: Xaa can be any proteinogenic amino acid
<220> FEATURE:
<221> NAME/KEY: MISC_FEATURE
<222> LOCATION: (10)..(10)
<223> OTHER INFORMATION: Xaa can be any proteinogenic amino acid
<220> FEATURE:
<221> NAME/KEY: MISC_FEATURE
<222> LOCATION: (13)..(13)
<223> OTHER INFORMATION: Xaa can be any proteinogenic amino acid
<220> FEATURE:
<221> NAME/KEY: MISC_FEATURE
<222> LOCATION: (16)..(16)
<223> OTHER INFORMATION: Xaa can be any proteinogenic amino acid
<220> FEATURE:
<221> NAME/KEY: MISC_FEATURE
<222> LOCATION: (19)..(19)
<223> OTHER INFORMATION: Xaa can be any proteinogenic amino acid

<400> SEQUENCE: 4

Trp Ser Xaa Ile Ala Xaa Xaa Leu Pro Xaa Arg Thr Xaa Asn Glu Xaa
1               5                   10                  15

Lys Asn Xaa Trp
            20

<210> SEQ ID NO 5
<211> LENGTH: 280
<212> TYPE: PRT
<213> ORGANISM: Artificial Sequence
<220> FEATURE:
<223> OTHER INFORMATION: Artificial Myb41 shortened protein

<400> SEQUENCE: 5

Met Gly Arg Ser Pro Cys Cys Asp Lys Asn Gly Val Lys Lys Gly Pro
1               5                   10                  15
```

```
Trp Thr Pro Glu Glu Asp Gln Lys Leu Ile Asp Tyr Ile Arg Phe His
            20                  25                  30

Gly Pro Gly Asn Trp Arg Ile Leu Pro Lys Asn Ala Gly Leu Gln Arg
        35                  40                  45

Cys Gly Lys Ser Cys Arg Leu Arg Trp Thr Asn Tyr Leu Arg Pro Asp
        50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
            115                 120                 125

Arg Leu Asp Leu Leu Asp Leu Ser Ser Leu Leu Ala Ala Leu Phe Asn
        130                 135                 140

Gln Pro Asn Phe Ser Ser Val Ala Thr His Ala Ser Ser Leu Leu Asn
145                 150                 155                 160

Pro Asp Val Leu Arg Leu Ala Ser Leu Leu Leu Pro Leu Gln Asn Pro
                165                 170                 175

Asn Pro Ile Tyr Pro Pro Asn Leu Asp Gln Asn Leu Gln Thr Pro Asn
                180                 185                 190

Thr Ser Ser Gln Asp Ser Gln Pro Gln Ala Glu Cys Thr Thr Pro Ser
            195                 200                 205

Asn Asp Glu Thr Ser Ser Phe Glu Pro Met Asn Ala Arg Leu Asp Val
        210                 215                 220

Gly Pro Ser Asp Val Leu Pro Pro Leu Ser Glu Ser Phe Asp Leu Asp
225                 230                 235                 240

Ser Leu Met Ser Thr Pro Met Ser Ser Pro Gln Gln Asn Ser Ile Glu
                245                 250                 255

Ala Glu Ala Asn Ser Ser Ser Phe Phe Asp Phe Gly Ile Pro Asp Asn
            260                 265                 270

Phe Ile Phe Asp Asp Phe Met Phe
        275                 280
```

```
<210> SEQ ID NO 6
<211> LENGTH: 282
<212> TYPE: PRT
<213> ORGANISM: Artificial Sequence
<220> FEATURE:
<223> OTHER INFORMATION: Phosphomimetic mutant of SEQ ID NO: 2

<400> SEQUENCE: 6
```

```
Met Gly Arg Ser Pro Cys Cys Asp Lys Asn Gly Val Lys Lys Gly Pro
1               5                   10                  15

Trp Thr Ala Glu Glu Asp Gln Lys Leu Ile Asp Tyr Ile Arg Phe His
            20                  25                  30

Gly Pro Gly Asn Trp Arg Thr Leu Pro Lys Asn Ala Gly Leu His Arg
        35                  40                  45

Cys Gly Lys Ser Cys Arg Leu Arg Trp Thr Asn Tyr Leu Arg Pro Asp
        50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                85                  90                  95
```

-continued

```
Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
            115                 120                 125

Arg Leu Asp Leu Leu Asp Leu Ser Ser Leu Leu Ser Ala Leu Phe Asn
            130                 135                 140

Gln Pro Asn Phe Ser Ala Val Ala Thr His Ala Ser Ser Leu Leu Asn
145                 150                 155                 160

Pro Asp Val Leu Arg Leu Ala Ser Leu Leu Leu Pro Leu Gln Asn Pro
                165                 170                 175

Asn Pro Val Tyr Pro Ser Asn Leu Asp Gln Asn Leu Gln Thr Pro Asn
                180                 185                 190

Thr Ser Ser Glu Ser Ser Gln Pro Gln Ala Glu Thr Ser Thr Val Pro
                195                 200                 205

Thr Asn Tyr Glu Thr Ser Ser Leu Glu Pro Met Asn Ala Arg Leu Asp
            210                 215                 220

Asp Val Gly Leu Ala Asp Val Leu Pro Pro Leu Ser Glu Ser Phe Asp
225                 230                 235                 240

Leu Asp Ser Leu Met Ser Thr Pro Met Ser Asp Pro Arg Gln Asn Ser
                245                 250                 255

Ile Glu Ala Glu Thr Asn Ser Ser Thr Phe Phe Asp Phe Gly Ile Pro
            260                 265                 270

Glu Asp Phe Ile Leu Asp Asp Phe Met Phe
            275                 280
```

```
<210> SEQ ID NO 7
<211> LENGTH: 282
<212> TYPE: PRT
<213> ORGANISM: Artificial Sequence
<220> FEATURE:
<223> OTHER INFORMATION: Phosphomimetic mutant of SEQ ID NO: 2

<400> SEQUENCE: 7
```

```
Met Gly Arg Ser Pro Cys Cys Asp Lys Asn Gly Val Lys Lys Gly Pro
1               5                   10                  15

Trp Thr Ala Glu Glu Asp Gln Lys Leu Ile Asp Tyr Ile Arg Phe His
            20                  25                  30

Gly Pro Gly Asn Trp Arg Thr Leu Pro Lys Asn Ala Gly Leu His Arg
            35                  40                  45

Cys Gly Lys Ser Cys Arg Leu Arg Trp Thr Asn Tyr Leu Arg Pro Asp
            50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
            115                 120                 125

Arg Leu Asp Leu Leu Asp Leu Ser Ser Leu Leu Ser Ala Leu Phe Asn
            130                 135                 140

Gln Pro Asn Phe Ser Ala Val Ala Thr His Ala Ser Ser Leu Leu Asn
145                 150                 155                 160

Pro Asp Val Leu Arg Leu Ala Ser Leu Leu Leu Pro Leu Gln Asn Pro
                165                 170                 175
```

-continued

```
Asn Pro Val Tyr Pro Ser Asn Leu Asp Gln Asn Leu Gln Thr Pro Asn
            180                 185                 190

Thr Ser Ser Glu Ser Ser Gln Pro Gln Ala Glu Thr Ser Thr Val Pro
            195                 200                 205

Thr Asn Tyr Glu Thr Ser Ser Leu Glu Pro Met Asn Ala Arg Leu Asp
            210                 215                 220

Asp Val Gly Leu Ala Asp Val Leu Pro Pro Leu Ser Glu Ser Phe Asp
225                 230                 235                 240

Leu Asp Ser Leu Met Ser Thr Pro Met Ser Glu Pro Arg Gln Asn Ser
                245                 250                 255

Ile Glu Ala Glu Thr Asn Ser Ser Thr Phe Phe Asp Phe Gly Ile Pro
            260                 265                 270

Glu Asp Phe Ile Leu Asp Asp Phe Met Phe
            275                 280
```

<210> SEQ ID NO 8
<211> LENGTH: 280
<212> TYPE: PRT
<213> ORGANISM: Artificial Sequence
<220> FEATURE:
<223> OTHER INFORMATION: Phosphomimetic mutant of SEQ ID NO: 5

<400> SEQUENCE: 8

```
Met Gly Arg Ser Pro Cys Cys Asp Lys Asn Gly Val Lys Lys Gly Pro
1               5                   10                  15

Trp Thr Pro Glu Glu Asp Gln Lys Leu Ile Asp Tyr Ile Arg Phe His
            20                  25                  30

Gly Pro Gly Asn Trp Arg Ile Leu Pro Lys Asn Ala Gly Leu Gln Arg
            35                  40                  45

Cys Gly Lys Ser Cys Arg Leu Arg Trp Thr Asn Tyr Leu Arg Pro Asp
        50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
            115                 120                 125

Arg Leu Asp Leu Leu Asp Leu Ser Ser Leu Leu Ala Ala Leu Phe Asn
            130                 135                 140

Gln Pro Asn Phe Ser Ser Val Ala Thr His Ala Ser Ser Leu Leu Asn
145                 150                 155                 160

Pro Asp Val Leu Arg Leu Ala Ser Leu Leu Leu Pro Leu Gln Asn Pro
                165                 170                 175

Asn Pro Ile Tyr Pro Pro Asn Leu Asp Gln Asn Leu Gln Thr Pro Asn
            180                 185                 190

Thr Ser Ser Gln Asp Ser Gln Pro Gln Ala Glu Cys Thr Thr Pro Ser
            195                 200                 205

Asn Asp Glu Thr Ser Ser Phe Glu Pro Met Asn Ala Arg Leu Asp Val
            210                 215                 220

Gly Pro Ser Asp Val Leu Pro Pro Leu Ser Glu Ser Phe Asp Leu Asp
225                 230                 235                 240

Ser Leu Met Ser Thr Pro Met Ser Asp Pro Gln Gln Asn Ser Ile Glu
                245                 250                 255
```

-continued

```
Ala Glu Ala Asn Ser Ser Ser Phe Phe Asp Phe Gly Ile Pro Asp Asn
            260                 265                 270

Phe Ile Phe Asp Asp Phe Met Phe
        275                 280

<210> SEQ ID NO 9
<211> LENGTH: 280
<212> TYPE: PRT
<213> ORGANISM: Artificial Sequence
<220> FEATURE:
<223> OTHER INFORMATION: Phosphomimetic mutant of SEQ ID NO: 5

<400> SEQUENCE: 9

Met Gly Arg Ser Pro Cys Cys Asp Lys Asn Gly Val Lys Lys Gly Pro
1               5                   10                  15

Trp Thr Pro Glu Glu Asp Gln Lys Leu Ile Asp Tyr Ile Arg Phe His
            20                  25                  30

Gly Pro Gly Asn Trp Arg Ile Leu Pro Lys Asn Ala Gly Leu Gln Arg
        35                  40                  45

Cys Gly Lys Ser Cys Arg Leu Arg Trp Thr Asn Tyr Leu Arg Pro Asp
    50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
        115                 120                 125

Arg Leu Asp Leu Leu Asp Leu Ser Ser Leu Leu Ala Ala Leu Phe Asn
    130                 135                 140

Gln Pro Asn Phe Ser Ser Val Ala Thr His Ala Ser Ser Leu Leu Asn
145                 150                 155                 160

Pro Asp Val Leu Arg Leu Ala Ser Leu Leu Leu Pro Leu Gln Asn Pro
                165                 170                 175

Asn Pro Ile Tyr Pro Pro Asn Leu Asp Gln Asn Leu Gln Thr Pro Asn
            180                 185                 190

Thr Ser Ser Gln Asp Ser Gln Pro Gln Ala Glu Cys Thr Thr Pro Ser
        195                 200                 205

Asn Asp Glu Thr Ser Ser Phe Glu Pro Met Asn Ala Arg Leu Asp Val
    210                 215                 220

Gly Pro Ser Asp Val Leu Pro Pro Leu Ser Glu Ser Phe Asp Leu Asp
225                 230                 235                 240

Ser Leu Met Ser Thr Pro Met Ser Glu Pro Gln Gln Asn Ser Ile Glu
                245                 250                 255

Ala Glu Ala Asn Ser Ser Ser Phe Phe Asp Phe Gly Ile Pro Asp Asn
            260                 265                 270

Phe Ile Phe Asp Asp Phe Met Phe
        275                 280

<210> SEQ ID NO 10
<211> LENGTH: 217
<212> TYPE: PRT
<213> ORGANISM: Artificial Sequence
<220> FEATURE:
<223> OTHER INFORMATION: Synthetic polypeptide
```

```
<400> SEQUENCE: 10

Leu Leu Asp Asn Asn Glu Glu Leu Asn Arg Ala Ala Leu Thr Asn Gln
1               5                   10                  15

Lys Tyr Glu Ser Asn Ser Val Lys Lys Leu Arg Lys Ile Thr Leu Asp
                20                  25                  30

Asp Leu Leu Arg Ala Ile Leu Asn Ile Arg Thr Thr His Arg Gly Val
            35                  40                  45

Tyr Arg Ser Arg Leu Lys Lys Ala Leu Lys Met Ala Met Lys Leu Met
    50                  55                  60

Pro Phe Thr Asp Lys Pro Glu Val Met Lys Ile Thr Glu Ile Ile Ser
65                  70                  75                  80

Ser Ile Ile Ser Asn Ser Ser Leu Leu Ala Met Gln Gly Asn Ser Gln
                85                  90                  95

Ala Cys Met His Lys Gly Leu Trp Lys Pro Glu Glu Ser Phe Ser Asp
                100                 105                 110

Glu Gly Phe Lys Arg Leu Thr Ala Ser Asp Ile Lys Arg Ser Ile Asp
            115                 120                 125

Glu Glu Ile Lys Thr Ile Glu Leu His Ala Leu Ala Leu Ser Leu Ser
    130                 135                 140

Ser Pro Thr Thr Lys Asn Ile Lys Asn Tyr Leu Asp Leu Ile Lys Lys
145                 150                 155                 160

Lys Val Asp Glu Met Ser Leu Ala Tyr Ala Val His Ser Asp Asn Asn
                165                 170                 175

Ala Leu Glu Cys Gln Leu Val Leu Pro Trp Leu Val Tyr Thr Gly Arg
                180                 185                 190

Asp Asn Glu Arg Asp Thr Phe Pro Phe Asp Leu Glu Glu Phe Asp Glu
            195                 200                 205

Asp Leu Thr Leu Ala Glu Ile Phe Leu
    210                 215

<210> SEQ ID NO 11
<211> LENGTH: 192
<212> TYPE: PRT
<213> ORGANISM: Artificial Sequence
<220> FEATURE:
<223> OTHER INFORMATION: Synthetic polypeptide

<400> SEQUENCE: 11

Asn Pro Asn Glu Asn Glu Ser Ser Gly Lys Ile Leu Ser Leu His Ser
1               5                   10                  15

Thr Ser His Thr Leu His Glu Asn Gln Arg Ile Leu Trp Lys Gly Phe
                20                  25                  30

Thr Val Gly His Met Ile His Cys Asp Ser Asn Ser Asp Gln Lys Lys
            35                  40                  45

Gln His Ser Gly Ile Pro Ala Met Ala Phe Ser Lys Arg Val Met Leu
    50                  55                  60

Gly Gly Cys Lys Gln Met Asn Ala Gly Ala Arg Cys Ala Cys Asn Val
65                  70                  75                  80

Lys Gln Asn Ala Ile Thr Ala Leu Phe Lys Met Ala Lys Ala Asp Leu
                85                  90                  95

Gly Leu Asn Phe Arg Thr Ser Val Glu Ser Gln Phe Glu Met Ser Thr
                100                 105                 110

Leu Ile Thr Asn Asn Thr Glu Val Asn Gly His Thr Pro Ala Arg Val
            115                 120                 125

Asp Gly Glu Asp Asn Trp Asn Ser Gln Asp Asn Gln Met Gly Leu His
```

-continued

```
                130                   135                   140

Ala His Glu Ala Lys Arg Thr Asp Met Arg Leu Gly Met Asn Tyr Glu
145                 150                   155                   160

Lys Met Ile Arg Arg Asn Ala Ala Asn Thr Asp Thr His Ser Cys Lys
                165                   170                   175

Thr Glu Ile Leu Arg Leu Ala Ala Ser Asp Ile Glu Ser His Leu Gly
            180                   185                   190

<210> SEQ ID NO 12
<211> LENGTH: 172
<212> TYPE: PRT
<213> ORGANISM: Artificial Sequence
<220> FEATURE:
<223> OTHER INFORMATION: Synthetic polypeptide

<400> SEQUENCE: 12

Ile Gln Val Asn Lys Ile Glu Tyr Ile Ile Arg Gln Leu Arg Arg Met
1               5                   10                  15

Lys Gln Cys Glu Ala Ile Val Arg Glu Lys Asn Asn Leu Ser Gln Thr
            20                  25                  30

Ser Val Thr Lys Ser Arg Pro Val Lys Ser Thr Glu Thr Asp Lys Pro
        35                  40                  45

Gly Phe Val Asp Lys His His Thr Asp Cys His Trp Ile Arg Gly Leu
    50                  55                  60

Gly Gly Arg Phe Arg Leu Glu Pro Gly Asp Gln Asn Thr Ile Arg His
65                  70                  75                  80

Lys Ala Leu Thr Val Cys Glu Gln Gln Ala Ile Ile Arg Asn Gln Ala
                85                  90                  95

Arg Ser Val Leu Ile Ser Asp Arg Ser Asn Gly Ser Ala Ala Cys Tyr
            100                 105                 110

His Glu Gly His Val Thr Glu Gln Phe Thr Ala Lys Lys Lys His Asn
        115                 120                 125

His Lys Leu Thr Asp Thr Gln Ala Arg Pro Lys Gly Ala Ala Ile Thr
    130                 135                 140

Lys Arg Asn Arg Met Lys Glu Val Lys Ser Gln Gly Phe Asn Lys Lys
145                 150                 155                 160

Met Asn Arg Val Ile Ser Ala Lys Ala Pro Ser Asn
                165                 170

<210> SEQ ID NO 13
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 13

Asn Tyr Ser Lys Gln Val Ala Ser Val Tyr Arg Ala His Cys Asn Ser
1               5                   10                  15

His Leu Arg Val Gln Glu Met Thr Pro Gln Val Asn Asn Val Glu Asn
            20                  25                  30

Ala Ala Thr Lys Lys Asp Glu Glu Arg Glu Lys Asp Glu Thr His Ile
        35                  40                  45

Ser Asn Thr Arg Ile Ser Lys Gln Gln Ala Leu Ile Thr Ala Thr Ser
    50                  55                  60

Arg Ser Gly Glu Lys Ser Asp Asp Leu Cys Ile Cys Ala Asn Gln Thr
65                  70                  75                  80
```

```
Asn Ala Met Arg Val Cys Ile Phe Gln Ile Gly Thr Gln Leu Gly Arg
                85                  90                  95

Ser Val Leu Gly Asn Ile Lys Ile Lys His Arg Thr Lys Glu His Asn
            100                 105                 110

Ala Ser Leu Glu Leu Gln Asp Gln Thr Cys Met Ser Glu His Leu Asn
        115                 120                 125

Trp Ala Gln Thr Glu Val Arg Asn Asn Pro Tyr Tyr Arg
    130                 135                 140

<210> SEQ ID NO 14
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 14

Ala Ser Val Phe Gln Asn Arg Leu Arg Thr Gln Val Gln Gln Gln Met
1               5                   10                  15

Arg Lys Tyr Arg Gly Lys Gly Val Ile Asn Glu Pro Val Asn Lys Val
            20                  25                  30

Thr Ser Thr Arg Glu Met Ala Asp Tyr His Glu Pro Asn Pro Glu Glu
        35                  40                  45

Thr Thr Asn Ile Tyr Asn Ser Ser Val Asn Gln Val His Arg Ser Thr
        50                  55                  60

Asn Ser Trp Arg Asp Tyr Asn Thr Ser Thr Ile Ser Ser Leu Pro Gly
65                  70                  75                  80

Lys Ser Asn Val Asn Glu Leu Cys Gly Val Asp Gly Gly Val Pro Arg
                85                  90                  95

Asn Thr Leu Leu Pro Met Pro Leu Gly Val
            100                 105

<210> SEQ ID NO 15
<211> LENGTH: 55
<212> TYPE: PRT
<213> ORGANISM: Artificial Sequence
<220> FEATURE:
<223> OTHER INFORMATION: Synthetic polypeptide

<400> SEQUENCE: 15

Glu Val Ala Val Arg Ser Gln Thr Asn Ser Trp Ser Asn Asn Thr Pro
1               5                   10                  15

Gln Pro Asn Gln Asp Pro His Pro Gly Pro Pro Tyr Thr Ala Gln Val
            20                  25                  30

Val Tyr Arg Asn Ile Met Pro Ser Gly Asn Ile Lys His Asn Asn Tyr
        35                  40                  45

Tyr Asn Met Ser Gln Ser Tyr
    50                  55

<210> SEQ ID NO 16
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 16

Met His Val Ser Thr Val Thr Ser Val Gln Met Leu Pro Glu Ser Gln
1               5                   10                  15

Lys Pro Lys Thr Thr Pro Asn Asn Trp Thr Ser Cys
```

-continued

```
           20                    25

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 17

Ile Tyr Thr Gln Val Ile Ser Gln Tyr
1               5

<210> SEQ ID NO 18

<400> SEQUENCE: 18

000

<210> SEQ ID NO 19
<211> LENGTH: 282
<212> TYPE: PRT
<213> ORGANISM: Arabidopsis thaliana

<400> SEQUENCE: 19

Met Gly Arg Ser Pro Cys Cys Asp Lys Asn Gly Val Lys Lys Gly Pro
1               5                   10                  15

Trp Thr Ala Glu Glu Asp Gln Lys Leu Ile Asp Tyr Ile Arg Phe His
            20                  25                  30

Gly Pro Gly Asn Trp Arg Thr Leu Pro Lys Asn Ala Gly Leu His Arg
        35                  40                  45

Cys Gly Lys Ser Cys Arg Leu Arg Trp Thr Asn Tyr Leu Arg Pro Asp
    50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
        115                 120                 125

Arg Leu Asp Leu Leu Asp Leu Ser Ser Leu Leu Ser Ala Leu Phe Asn
    130                 135                 140

Gln Pro Asn Phe Ser Ala Val Ala Thr His Ala Ser Ser Leu Leu Asn
145                 150                 155                 160

Pro Asp Val Leu Arg Leu Ala Ser Leu Leu Leu Pro Leu Gln Asn Pro
                165                 170                 175

Asn Pro Val Tyr Pro Ser Asn Leu Asp Gln Asn Leu Gln Thr Pro Asn
            180                 185                 190

Thr Ser Ser Glu Ser Ser Gln Pro Gln Ala Glu Thr Ser Thr Val Pro
        195                 200                 205

Thr Asn Tyr Glu Thr Ser Ser Leu Glu Pro Met Asn Ala Arg Leu Asp
    210                 215                 220

Asp Val Gly Leu Ala Asp Val Leu Pro Pro Leu Ser Glu Ser Phe Asp
225                 230                 235                 240

Leu Asp Ser Leu Met Ser Thr Pro Met Ser Ser Pro Arg Gln Asn Ser
                245                 250                 255

Ile Glu Ala Glu Thr Asn Ser Ser Thr Phe Phe Asp Phe Gly Ile Pro
```

```
            260               265               270

Glu Asp Phe Ile Leu Asp Asp Phe Met Phe
        275               280
```

<210> SEQ ID NO 20
<211> LENGTH: 323
<212> TYPE: PRT
<213> ORGANISM: Glycine max

<400> SEQUENCE: 20

```
Met Gly Arg Val Pro Cys Cys Asp Lys Asn Gly Leu Lys Lys Gly Pro
1               5                   10                  15

Trp Thr Pro Glu Glu Asp Leu Lys Leu Thr Asn Tyr Ile Gln Phe His
            20                  25                  30

Gly Pro Gly Asn Trp Arg Ser Leu Pro Lys Asn Ala Gly Leu Lys Arg
        35                  40                  45

Cys Gly Lys Ser Cys Arg Leu Arg Trp Thr Asn Tyr Leu Arg Pro Asp
    50                  55                  60

Ile Lys Arg Gly Arg Phe Ser Leu Glu Glu Glu Asp Ile Ile Ile Gln
65                  70                  75                  80

Leu His Ser Ile Leu Gly Asn Lys Trp Ser Ala Ile Ala Ser Arg Leu
                85                  90                  95

Pro Gly Arg Thr Asp Asn Glu Ile Lys Asn Tyr Trp Asn Thr His Ile
            100                 105                 110

Arg Lys Arg Leu Leu Arg Met Gly Ile Asp Pro Val Thr His Thr Pro
            115                 120                 125

Arg Leu Asp Leu Leu Asp Met Ser Ser Ile Leu Arg Ser Val Phe Gly
        130                 135                 140

Lys Pro Ser Leu Leu Asn Met Gln Gly Leu Leu Arg Ala Gln Ala Leu
145                 150                 155                 160

Met Asn Gln Gly Leu Leu Lys Leu Ala Ser Thr Ala Ser Leu Leu Ser
                165                 170                 175

Thr Ile Asn Asn Asp Glu Asn Pro Asn Leu Ala Ser His Asn Tyr Val
            180                 185                 190

Gln Asn Gln Val Thr Thr Pro Pro Ser Leu Asp Ser Ala Gln Phe Gln
        195                 200                 205

Phe Gln Met Pro Thr Thr Gln Thr Asn Asn Val Glu Val Phe Ser Gly
        210                 215                 220

Thr Val Ala Asn Leu Ser Cys Ser Ser Ser Pro Ser Gly Asp Glu Asn
225                 230                 235                 240

Leu Val Leu Gln Gln Asn Gln Val Gly Leu Ser Gly Asn His Asp Ala
                245                 250                 255

Leu Val His Ser Leu Asn Asn Ala Asn Gln Asn Met Glu Cys Asp Ser
            260                 265                 270

Val Leu Pro Thr Pro Val Ser Ser Pro Asn Arg Leu Asn Ser Ser Ser
        275                 280                 285

Asn Tyr Val Arg Ser Gly Thr Asp Glu Glu Arg Asp Ser Phe Phe Ser
        290                 295                 300

Asp Leu Phe Glu Phe Glu Ile Pro Glu Ser Leu Asp Asp Ile Ala Asp
305                 310                 315                 320

Ile Phe Leu
```

<210> SEQ ID NO 21
<211> LENGTH: 323
<212> TYPE: PRT

```
<213> ORGANISM: Glycine soja

<400> SEQUENCE: 21

Met Gly Arg Val Pro Cys Cys Asp Lys Asn Gly Leu Lys Lys Gly Pro
1               5                   10                  15

Trp Thr Pro Glu Glu Asp Leu Lys Leu Thr Asn Tyr Ile Gln Phe His
            20                  25                  30

Gly Pro Gly Asn Trp Arg Ser Leu Pro Lys Asn Ala Gly Leu Lys Arg
        35                  40                  45

Cys Gly Lys Ser Cys Arg Leu Arg Trp Thr Asn Tyr Leu Arg Pro Asp
    50                  55                  60

Ile Lys Arg Gly Arg Phe Ser Leu Glu Glu Glu Asp Ile Ile Ile Gln
65                  70                  75                  80

Leu His Ser Ile Leu Gly Asn Lys Trp Ser Ala Ile Ala Ser Arg Leu
                85                  90                  95

Pro Gly Arg Thr Asp Asn Glu Ile Lys Asn Tyr Trp Asn Thr His Ile
            100                 105                 110

Arg Lys Arg Leu Leu Arg Met Gly Ile Asp Pro Val Thr His Thr Pro
            115                 120                 125

Arg Leu Asp Leu Leu Asp Met Ser Ser Ile Leu Arg Ser Val Phe Gly
        130                 135                 140

Asn Pro Ser Leu Leu Asn Met Gln Gly Leu Leu Arg Ala Gln Ala Leu
145                 150                 155                 160

Met Asn Gln Gly Leu Leu Lys Leu Ala Ser Thr Ala Ser Leu Leu Ser
                165                 170                 175

Thr Ile Asn Asn Asp Glu Asn Pro Asn Leu Ala Ser His Asn Tyr Val
                180                 185                 190

Gln Asn Gln Val Thr Thr Pro Pro Ser Leu Asp Ser Ala Gln Phe Gln
            195                 200                 205

Phe Gln Met Pro Thr Thr Gln Thr Asn Asn Val Glu Val Phe Ser Gly
        210                 215                 220

Thr Val Ala Asn Leu Ser Cys Ser Ser Ser Pro Ser Gly Asp Glu Asn
225                 230                 235                 240

Leu Val Leu Gln Gln Asn Gln Val Gly Leu Ser Gly Asn His Asp Ala
                245                 250                 255

Leu Val His Ser Leu Asn Asn Ala Asn Gln Asn Met Glu Cys Asp Ser
                260                 265                 270

Val Leu Pro Thr Pro Val Ser Ser Pro Asn Arg Leu Asn Ser Ser Ser
            275                 280                 285

Asn Tyr Val Arg Ser Gly Thr Asp Glu Glu Arg Asp Ser Phe Phe Ser
        290                 295                 300

Asp Leu Phe Glu Phe Glu Ile Pro Glu Ser Leu Asp Asp Ile Ala Asp
305                 310                 315                 320

Ile Phe Leu

<210> SEQ ID NO 22
<211> LENGTH: 337
<212> TYPE: PRT
<213> ORGANISM: Glycine soja

<400> SEQUENCE: 22

Met Gly Arg Ala Pro Cys Cys Asp Glu Asn Gly Leu Lys Lys Gly Pro
1               5                   10                  15

Trp Thr Pro Glu Glu Asp Leu Lys Leu Thr Asn Tyr Ile Gln Ile His
            20                  25                  30
```

```
Gly Pro Gly Asn Trp Arg Ser Leu Pro Lys Asn Ala Gly Leu Arg Arg
        35                  40                  45

Cys Gly Lys Ser Cys Arg Leu Arg Trp Thr Asn Tyr Leu Arg Pro Asp
    50                  55                  60

Ile Lys Arg Gly Arg Phe Ser Leu Glu Glu Glu Asp Val Ile Ile Gln
65                  70                  75                  80

Leu His Ser Ile Leu Gly Asn Lys Trp Ser Ala Ile Ala Ala Arg Leu
                85                  90                  95

Pro Gly Arg Thr Asp Asn Glu Ile Lys Asn Tyr Trp Asn Thr His Ile
            100                 105                 110

Arg Lys Arg Leu Leu Arg Met Gly Ile Asp Pro Val Thr His Thr Pro
        115                 120                 125

Arg Leu Asp Leu Leu Asp Met Ser Ser Ile Leu Arg Ser Met Leu Gly
    130                 135                 140

Asn Pro Ser Leu Leu Asn Met Gln Gly Leu Leu Gly Ala Gln Val Leu
145                 150                 155                 160

Met Asn Gln Gly Leu Leu Lys Leu Ala Ser Thr Ala Ser Leu Leu Ser
                165                 170                 175

Thr Ile Asn Asn Asp Glu Asn Pro Asn Leu Ala Ser Gln Asn Phe Val
            180                 185                 190

His Ser Gln Val Ala Thr Thr Pro Pro Ser Leu Asp Ser Thr Gln Phe
        195                 200                 205

Gln Phe Gln Met Pro Thr Asn Gln Thr Asn Asn Val Glu Val Glu Gly
    210                 215                 220

Phe Leu Gly Thr Val Thr Asn Leu Ser Cys Ser Ser Ser Pro Ser Gly
225                 230                 235                 240

Asp Asp Lys Ile Asn Leu Val Leu Gln Gln Lys Asn Gln Val Asp Leu
                245                 250                 255

Leu Gly Asn His Asp Val Leu Val His Ser Leu Tyr Asn Ala Lys Asn
            260                 265                 270

Gln Asn Met Gly Cys Asp Ser Val Met Arg Thr Pro Val Ser Ser Pro
        275                 280                 285

Asn Arg Leu Asn Ser Ser Ser Asn Tyr Val Lys Ser Gly Thr Glu Glu
    290                 295                 300

Glu Arg Glu Ser Phe Cys Ser Asp Leu Phe Glu Phe Glu Ile Pro Glu
305                 310                 315                 320

Ser Leu Asp Phe Ala Asp Ile Phe Cys Asn Val Pro Tyr Thr Pro Ile
                325                 330                 335

Asn
```

```
<210> SEQ ID NO 23
<211> LENGTH: 344
<212> TYPE: PRT
<213> ORGANISM: Glycine max

<400> SEQUENCE: 23
```

```
Met Gly Arg Ser Pro Cys Cys Asp Lys Asn Gly Leu Lys Lys Gly Pro
1               5                   10                  15

Trp Thr Pro Glu Glu Asp Gln Lys Leu Phe Asp Tyr Ile Gln Lys His
            20                  25                  30

Gly Tyr Gly Asn Trp Arg Val Leu Pro Lys Asn Ala Gly Leu Gln Arg
        35                  40                  45

Cys Gly Lys Ser Cys Arg Leu Arg Trp Thr Asn Tyr Leu Arg Pro Asp
    50                  55                  60
```

-continued

```
Ile Lys Arg Gly Arg Phe Thr Leu Glu Glu Glu Thr Ile Ile Gln
65              70              75              80

Leu His Ser Ile Leu Gly Asn Lys Trp Ser Ala Ile Ala Thr Arg Leu
            85              90              95

Pro Gly Arg Thr Asp Asn Glu Ile Lys Asn Tyr Trp Asn Thr His Ile
            100             105             110

Arg Lys Arg Leu Leu Arg Met Gly Met Asp Pro Val Thr His Arg Pro
            115             120             125

Arg Leu Asp Leu Leu Asp Leu Ser Ser Ile Leu Ser Ser Ser Leu Tyr
        130             135             140

Gly Ser Thr Gln Met Asn Ile Gln Arg Leu Leu Gly Thr His Thr Val
145             150             155             160

Val Asn Pro Glu Val Leu Lys Leu Ala Ser Ser Leu Phe Pro Ser Gln
            165             170             175

Gln Arg Glu Asn Ile Asn Met Cys Ala Gln Asn Cys Glu Glu Asn Gln
            180             185             190

Leu Cys Asp Pro Gln Ile Gln Ser Gln Ile Pro His Asp Leu Ala Gln
            195             200             205

Glu Ala Leu Pro Phe Thr His Ala Gln Leu Val Glu Ser Asn Thr Met
        210             215             220

Asn Thr Tyr Pro Ser Ile Phe His Glu Ser Gly Phe Gln Gln His Tyr
225             230             235             240

Ser Gln Leu Ser Asp Leu His Tyr Asn Gly Ile Asp His Lys Ser Tyr
            245             250             255

Val Pro Gln Leu Pro Ser Tyr Asp Tyr Pro Pro Met Ser Glu Ser Ser
            260             265             270

Thr Tyr Asn Asn Ser Tyr Asn Asn Ser Asn Gln Asn Phe Ser Tyr Ala
            275             280             285

Ser Val Leu Ser Thr Pro Ser Ser Ser Pro Thr Pro Leu Asn Ser Asn
        290             295             300

Ser Thr Phe Val Lys Gly Ser Ser Ser Thr Glu Asp Glu Thr Glu Ser
305             310             315             320

Tyr Val Ser Ser Asn Asn Leu Leu Arg Phe Glu Ile Pro Asp Met Leu
            325             330             335

Arg Met Asn Glu Tyr Ser Tyr Asn
            340

<210> SEQ ID NO 24
<211> LENGTH: 281
<212> TYPE: PRT
<213> ORGANISM: Capsella rubella

<400> SEQUENCE: 24

Met Gly Arg Ser Pro Cys Cys Asp Lys Asn Gly Val Lys Lys Gly Pro
1               5               10              15

Trp Thr Ala Glu Glu Asp Gln Lys Leu Ile Asp Tyr Ile Arg Phe His
            20              25              30

Gly Pro Gly Asn Trp Arg Ile Leu Pro Lys Asn Ala Gly Leu Gln Arg
        35              40              45

Cys Gly Lys Ser Cys Arg Leu Arg Trp Thr Asn Tyr Leu Arg Pro Asp
        50              55              60

Ile Lys Arg Gly Arg Phe Ser Phe Glu Glu Glu Glu Thr Ile Ile Gln
65              70              75              80

Leu His Ser Val Met Gly Asn Lys Trp Ser Ala Ile Ala Ala Arg Leu
```

-continued

```
                85                    90                    95

Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
            115                 120                 125

Arg Leu Asp Leu Leu Asp Leu Ser Ser Leu Leu Ser Val Leu Leu Ser
    130                 135                 140

Gln Pro Asn Phe Ser Ser Val Ala Thr Gln Ala Ser Ser Leu Leu Asn
145                 150                 155                 160

Pro Asp Val Leu Arg Leu Ala Phe Leu Leu Phe Pro Leu Gln Asn Pro
                165                 170                 175

Asn Pro Ile Tyr Ser Pro Asn Leu Asp Gln Asn Leu Gln Thr Pro Ile
                180                 185                 190

Thr Ser Ser Glu Ser Ser Gln Pro Gln Thr Glu Ser Thr Thr Pro Thr
                195                 200                 205

Asn Asn Glu Thr Ser Ser Leu Glu Pro Met Asn Ala Arg Leu Asp Asp
    210                 215                 220

Val Gly Pro Val Asp Val Leu Pro Pro Leu Ser Glu Ser Phe Asp Leu
225                 230                 235                 240

Asp Ser Leu Met Ser Thr Pro Met Ser Ser Pro Gln Gln Lys Ser Ile
                245                 250                 255

Glu Ala Glu Ala Asn Pro Ser Ser Phe Phe Asp Phe Gly Phe Pro Asp
                260                 265                 270

Asp Phe Ile Leu Asp Asp Phe Met Phe
                275                 280

<210> SEQ ID NO 25
<211> LENGTH: 283
<212> TYPE: PRT
<213> ORGANISM: Arabidopsis lyrata

<400> SEQUENCE: 25

Met Gly Arg Ser Pro Cys Cys Asp Lys Asn Gly Val Lys Lys Gly Pro
1               5                   10                  15

Trp Thr Ala Glu Glu Asp Gln Lys Leu Ile Asp Tyr Ile Arg Phe His
            20                  25                  30

Gly Pro Gly Asn Trp Arg Ile Leu Pro Lys Asn Ala Gly Leu Gln Arg
            35                  40                  45

Cys Gly Lys Ser Cys Arg Leu Arg Trp Thr Asn Tyr Leu Arg Pro Asp
    50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Thr Arg Leu
                85                  90                  95

Pro Gly Arg Thr Asp Asn Glu Ile Lys Asn His Trp Asn Thr His Ile
            100                 105                 110

Arg Lys Arg Leu Ile Arg Ser Gly Ile Asp Pro Val Thr His Ser Pro
            115                 120                 125

Arg Leu Asp Leu Leu Asp Leu Ser Ser Leu Leu Gly Ala Leu Phe Asn
    130                 135                 140

Gln Pro Asn Phe Ser Ser Ala Ala Thr His Ala Ser Ser Leu Leu Asn
145                 150                 155                 160

Pro Asp Val Leu Arg Leu Ala Ser Leu Leu Leu Pro Gln Leu Gln Asn
                165                 170                 175
```

```
Pro Asn Pro Met Tyr Ala Ser Ser Asn Leu Asp Gln Asn Leu Gln Thr
            180                 185                 190

Pro Ile Thr Ser Ser Glu Cys Ser Gln Pro Gln Ala Glu Ser Thr Thr
            195                 200                 205

Pro Thr Asn Asn Glu Thr Ser Ser Phe Glu Leu Met Asn Ala Arg Leu
            210                 215                 220

Asp Asp Val Ala Ser Ala Asp Val Leu Pro Pro Leu Ser Glu Ser Phe
225                 230                 235                 240

Asp Leu Glu Ser Leu Met Ser Thr Pro Met Ser Ser Pro Gln Gln Asp
                    245                 250                 255

Ser Ile Glu Ala Gly Thr Asn Ser Ser Ser Phe Phe Asp Phe Gly Phe
            260                 265                 270

Pro Glu Asp Phe Ile Leu Asp Asp Phe Met Phe
            275                 280

<210> SEQ ID NO 26
<211> LENGTH: 288
<212> TYPE: PRT
<213> ORGANISM: Eutrema salsugineum

<400> SEQUENCE: 26

Met Gly Arg Ser Pro Cys Cys Asp Lys Asn Gly Val Lys Lys Gly Pro
1                   5                   10                  15

Trp Thr Pro Glu Glu Asp Gln Lys Leu Ile Asp Tyr Ile Arg Phe His
            20                  25                  30

Gly Pro Gly Asn Trp Arg Ile Leu Pro Lys Asn Ala Gly Leu Gln Arg
            35                  40                  45

Cys Gly Lys Ser Cys Arg Leu Arg Trp Thr Asn Tyr Leu Arg Pro Asp
        50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                    85                  90                  95

Pro Gly Arg Thr Asp Asn Glu Ile Lys Asn His Trp Asn Thr His Ile
            100                 105                 110

Arg Lys Arg Leu Ile Lys Ser Gly Ile Asp Pro Val Thr His Ser Pro
            115                 120                 125

Arg Leu Asp Leu Leu Asp Val Ser Ser Leu Leu Ala Ala Leu Phe Asn
        130                 135                 140

Gln Pro Asn Phe Ser Ala Val Ala Ala His Ala Ser Ser Leu Leu Asn
145                 150                 155                 160

Pro Asp Val Leu Arg Leu Ala Ser Leu Leu Leu Ala Pro Gln Gln Pro
                    165                 170                 175

Leu Gln Asn Pro Asn Pro Ile Tyr Ser Ser Asn Leu Asp Gln Tyr Leu
            180                 185                 190

Gln Thr Pro Val Thr Ser Val Ser Ser Gln Asp Ser Gln Pro Gln Ala
            195                 200                 205

Glu Cys Thr Ile Pro Thr Asn Asn Asp Gln Thr Ser Ser Phe Glu Ser
        210                 215                 220

Ile Asn Ala Lys Leu Asn Val Gly Pro Ala Asp Val Leu Pro Pro Leu
225                 230                 235                 240

Ser Glu Ser Leu Asp Leu Asp Ser Leu Met Ser Thr Pro Lys Ser Ser
                    245                 250                 255

Pro Gln Gln Asn Ser Thr Glu Ala Glu Ala Asn Ser Ser Ser Phe Phe
            260                 265                 270
```

-continued

```
Asp Phe Gly Phe Pro Asp Asn Phe Thr Phe Asp Glu Phe Met Leu Ile
        275                 280                 285

<210> SEQ ID NO 27
<211> LENGTH: 288
<212> TYPE: PRT
<213> ORGANISM: Brassica oleracea

<400> SEQUENCE: 27

Met Gly Arg Leu Pro Cys Cys Asp Lys Asn Gly Val Lys Lys Gly Pro
1               5                   10                  15

Trp Thr Pro Glu Glu Asp Gln Lys Leu Ile Asp Tyr Ile Arg Leu His
            20                  25                  30

Gly Pro Gly Asn Trp Arg Ile Leu Pro Lys Asn Ala Gly Leu Gln Arg
        35                  40                  45

Cys Gly Lys Ser Cys Arg Leu Arg Trp Thr Asn Tyr Leu Arg Pro Asp
    50                  55                  60

Ile Lys Arg Gly Arg Phe Ser Phe Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
            115                 120                 125

Arg Leu Asp Leu Leu Asp Leu Ser Ser Leu Leu Ala Ala Ile Phe Asn
        130                 135                 140

Gln Pro Asn Phe Ser Ser Val Ala Thr Asn Ala Ser Ser Leu Leu Asn
145                 150                 155                 160

Pro Asp Val Leu Arg Leu Ala Ser Leu Leu Leu Pro Pro Gln Gln Pro
                165                 170                 175

Leu Gln Asn Pro Asn Thr Leu Tyr Glu Ser Asn Leu Asp Gln Asn Leu
            180                 185                 190

Gln Thr Pro Asn Thr Ser Val Ser Ser Gln Asp Thr Gln Pro Gln Ala
            195                 200                 205

Glu Cys Thr Ala Pro Thr Lys Asp Glu Thr Ser Tyr Phe Glu Pro Met
    210                 215                 220

Asn Ala Arg Leu Glu Val Gly Pro Ser Asp Val Leu Pro Pro Leu Ser
225                 230                 235                 240

Glu Ser Phe Asp Leu Asp Ser Leu Met Ser Thr Pro Asn Tyr Ser Pro
                245                 250                 255

Gln Gln Asn Asn Ile Glu Ala Glu Ala Asn Ser Ser Ser Leu Phe Asp
            260                 265                 270

Phe Arg Phe Pro Asp Asn Phe Thr Phe Asp Asp Phe Met Gly Leu Leu
        275                 280                 285

<210> SEQ ID NO 28
<211> LENGTH: 288
<212> TYPE: PRT
<213> ORGANISM: Brassica campestris

<400> SEQUENCE: 28

Met Gly Arg Leu Pro Cys Cys Asp Lys Asn Gly Val Lys Lys Gly Pro
1               5                   10                  15

Trp Thr Pro Glu Glu Asp Gln Lys Leu Ile Asp Tyr Ile Arg Val His
            20                  25                  30
```

-continued

```
Gly Pro Gly Asn Trp Arg Ile Leu Pro Lys Asn Ala Gly Leu Gln Arg
        35                  40              45

Cys Gly Lys Ser Cys Arg Leu Arg Trp Thr Asn Tyr Leu Arg Pro Asp
    50                  55              60

Ile Lys Arg Gly Arg Phe Ser Phe Glu Glu Glu Glu Thr Ile Ile Gln
65                  70              75              80

Leu His Ser Val Met Gly Asn Lys Trp Ser Ala Ile Ala Ala Arg Leu
                85                  90              95

Pro Gly Arg Thr Asp Asn Glu Ile Lys Asn His Trp Asn Thr His Ile
            100             105             110

Arg Lys Arg Leu Val Arg Ser Gly Ile Asp Pro Val Thr His Ser Pro
            115             120             125

Arg Leu Asp Leu Leu Asp Leu Ser Ser Leu Leu Ala Ala Ile Phe Asn
        130             135             140

Gln Pro Asn Phe Ser Ser Val Ala Thr Asn Ala Ser Ser Leu Leu Asn
145             150             155             160

Pro Asp Val Leu Arg Leu Ala Ser Leu Leu Leu Arg Pro Gln Gln Pro
                165             170             175

Leu Gln Asn Pro Asn Thr Leu Tyr Glu Ser Asn Leu Asp Gln Asn Leu
            180             185             190

Gln Thr Pro Asn Thr Ser Val Ser Ser Gln Asp Thr Gln Pro Gln Ala
            195             200             205

Glu Cys Thr Ala Pro Thr Lys Asp Glu Thr Ser Tyr Phe Glu Pro Met
    210             215             220

Asn Ala Arg Leu Glu Asp Gly Pro Ser Asp Val Leu Pro Pro Leu Ser
225             230             235             240

Glu Ser Phe Asp Leu Asp Ser Leu Met Ser Ala Pro Asn Tyr Ser Pro
                245             250             255

Gln Gln Asn Asn Ile Glu Ala Glu Ala Asn Ser Ser Ser Leu Phe Asp
            260             265             270

Phe Arg Phe Pro Asp Asn Phe Thr Phe Asp Asp Phe Met Gly Leu Leu
        275             280             285
```

<210> SEQ ID NO 29
<211> LENGTH: 289
<212> TYPE: PRT
<213> ORGANISM: Brassica campestris

<400> SEQUENCE: 29

```
Met Gly Arg Leu Pro Cys Cys Asp Lys Asn Gly Val Lys Lys Gly Gln
1               5                   10              15

Trp Thr Pro Glu Glu Asp Gln Lys Leu Ile Asp Tyr Ile Arg Val His
            20                  25              30

Gly Pro Gly Asn Trp Arg Ile Leu Pro Lys Asn Ala Gly Leu Gln Arg
        35                  40              45

Cys Gly Lys Ser Cys Arg Leu Arg Trp Thr Asn Tyr Leu Arg Pro Asp
    50                  55              60

Ile Lys Arg Gly Arg Phe Ser Phe Glu Glu Glu Glu Thr Ile Ile Gln
65                  70              75              80

Leu His Ser Val Met Gly Asn Lys Trp Ser Ala Ile Ala Ala Arg Leu
                85                  90              95

Pro Gly Arg Thr Asp Asn Glu Ile Lys Asn His Trp Asn Thr His Ile
            100             105             110

Arg Lys Arg Leu Val Arg Ser Gly Ile Asp Pro Val Thr His Ser Pro
```

```
            115                 120                 125

Arg Leu Asp Leu Leu Asp Leu Ser Ser Leu Leu Ala Ala Ile Phe Asn
    130                 135                 140

Gln Pro Asn Phe Ser Ser Val Ala Thr Asn Ala Ser Ser Leu Leu Asn
145                 150                 155                 160

Pro Asp Val Leu Arg Leu Ala Ser Leu Leu Leu Pro Pro Gln Gln Pro
                    165                 170                 175

Leu Gln Lys Pro Asn Ala Leu Tyr Ala Ser Asn Leu Asp Gln Asn Leu
                180                 185                 190

Gln Thr Pro Asn Thr Ser Val Ser Ser Gln Asp Ser Gln Pro Gln Ala
                195                 200                 205

Glu Cys Thr Thr Pro Ala Lys Asp Glu Thr Ser Tyr Phe Glu Pro Ile
    210                 215                 220

Met Asn Ala Arg Leu Glu Val Gly Pro Ser Asp Val Leu Pro Pro Leu
225                 230                 235                 240

Ser Glu Ser Phe Asp Leu Asp Ser Leu Met Ser Thr Pro Asn Tyr Ser
                245                 250                 255

Pro Gln Gln Asn Asn Ile Glu Ala Glu Ala Asn Ser Ser Ser Leu Phe
                260                 265                 270

Asp Phe Arg Phe Pro Asp Asn Phe Thr Phe Asp Asp Phe Met Gly Leu
            275                 280                 285

Leu

<210> SEQ ID NO 30
<211> LENGTH: 288
<212> TYPE: PRT
<213> ORGANISM: Brassica napus

<400> SEQUENCE: 30

Met Gly Arg Leu Pro Cys Cys Asp Lys Asn Gly Val Lys Lys Gly Pro
1               5                   10                  15

Trp Thr Pro Glu Glu Asp Gln Lys Leu Ile Asp Tyr Ile Arg Leu His
                20                  25                  30

Gly Pro Gly Asn Trp Arg Ile Leu Pro Lys Asn Ala Gly Leu Gln Arg
            35                  40                  45

Cys Gly Lys Ser Cys Arg Leu Arg Trp Thr Asn Tyr Leu Arg Pro Asp
    50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
                100                 105                 110

Arg Lys Arg Leu Val Arg Ser Gly Ile Asp Pro Val Thr His Ser Pro
            115                 120                 125

Arg Leu Gly Leu Pro Asp Leu Ser Ser Leu Leu Ala Ala Ile Phe Asn
    130                 135                 140

Gln Pro Asn Phe Ser Ser Val Ala Thr Asn Ala Ser Ser Leu Phe Asn
145                 150                 155                 160

Leu Asp Val Leu Arg Leu Ala Ser Leu Leu Leu Pro Pro Gln Gln Pro
                    165                 170                 175

Leu Gln Asn Pro Asn Thr Leu Tyr Glu Ser Asn Leu Asp Gln Asn Leu
                180                 185                 190

Gln Thr Pro Asn Thr Ser Val Ser Ser Gln Gly Thr Gln Pro Gln Ala
```

-continued

```
             195                 200                 205

Glu Cys Thr Ala Pro Thr Lys Asp Glu Thr Ser Tyr Phe Glu Pro Met
    210                 215                 220

Asn Ala Arg Leu Glu Val Gly Pro Ser Asp Val Leu Pro Pro Leu Ser
225                 230                 235                 240

Glu Ser Phe Asp Leu Asp Ser Leu Met Ser Thr Pro Asn Tyr Ser Pro
                245                 250                 255

Gln Gln Asn Asn Ile Glu Ala Glu Ala Asn Ser Ser Ser Leu Phe Asp
                260                 265                 270

Phe Arg Phe Pro Asp Asn Phe Thr Phe Asp Asp Phe Met Gly Leu Leu
        275                 280                 285

<210> SEQ ID NO 31
<211> LENGTH: 285
<212> TYPE: PRT
<213> ORGANISM: Brassica oleracea

<400> SEQUENCE: 31

Met Gly Arg Ser Pro Cys Cys Asp Lys Asn Gly Val Lys Lys Gly Pro
1               5                   10                  15

Trp Thr Ser Glu Glu Asp Gln Lys Leu Ile Asp Tyr Ile Arg Phe His
                20                  25                  30

Gly Pro Gly Asn Trp Arg Thr Leu Pro Lys Asn Ala Gly Leu Gln Arg
            35                  40                  45

Cys Gly Lys Ser Cys Arg Leu Arg Trp Thr Asn Tyr Leu Arg Pro Asp
    50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
                100                 105                 110

Arg Lys Arg Leu Val Arg Ser Gly Ile Asp Pro Val Thr His Ser Pro
        115                 120                 125

Arg Leu Asp Leu Leu Asp Ile Ser Ser Leu Leu Ala Ala Leu Ile Asn
    130                 135                 140

Gln Pro Asn Phe Ser Ser Val Ala Thr His Ala Ser Ser Leu Leu His
145                 150                 155                 160

Pro Asp Val Leu Arg Leu Ala Ser Leu Leu Leu Pro Pro Gln Gln Pro
                165                 170                 175

Leu Gln Asp Phe Asn Pro Ile Tyr Ala Pro Asn Leu Asp Gln Asn Ile
                180                 185                 190

Gln Thr Pro Ile Thr Thr Val Ser Ser Gln Asp Ser Gln Leu Gln Ala
            195                 200                 205

Glu Cys Thr Thr Pro Val Ser Asn Asn Glu Thr Ser Ser Phe Asp Pro
    210                 215                 220

Phe Met Lys Ala Arg Leu Glu Val Ser His Glu Asp Val Leu Pro Pro
225                 230                 235                 240

Leu Ser Glu Ser Phe Asp Leu Glu Ser Leu Met Ser Thr Pro Gln Gln
                245                 250                 255

Asn Ser Ile Glu Ala Glu Ala Asn Ser Ser Ser Phe Phe Asp Phe Gly
            260                 265                 270

Phe Pro Asp Asn Phe Thr Leu Glu Glu Phe Met Leu Asn
        275                 280                 285
```

-continued

```
<210> SEQ ID NO 32
<211> LENGTH: 285
<212> TYPE: PRT
<213> ORGANISM: Brassica napus

<400> SEQUENCE: 32

Met Gly Arg Ser Pro Cys Cys Asp Lys Asn Gly Val Lys Lys Gly Pro
1               5                   10                  15

Trp Thr Ser Glu Glu Asp Gln Lys Leu Ile Asp Tyr Ile Arg Phe His
            20                  25                  30

Gly Pro Gly Asn Trp Arg Thr Leu Pro Lys Asn Ala Gly Leu Gln Arg
        35                  40                  45

Cys Gly Lys Ser Cys Arg Leu Arg Trp Thr Asn Tyr Leu Arg Pro Asp
    50                  55                  60

Ile Lys Arg Gly Arg Phe Ser Phe Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
        115                 120                 125

Arg Leu Asp Leu Leu Asp Ile Ser Ser Leu Leu Val Ala Leu Ile Asn
    130                 135                 140

Gln Pro Asn Phe Ser Ser Val Ala Thr His Ala Ser Ser Leu Leu His
145                 150                 155                 160

Pro Asp Val Leu Arg Leu Ala Ser Leu Leu Leu Pro Pro Gln Gln Pro
                165                 170                 175

Leu Gln Asp Phe Asn Pro Ile Tyr Ala Pro Asn Leu Asp Gln Asn Ile
            180                 185                 190

Gln Thr Pro Ile Thr Thr Val Ser Ser Gln Asp Ser Gln Leu Gln Ala
        195                 200                 205

Glu Cys Thr Thr Pro Val Ser Asn Asn Glu Thr Ser Ser Phe Asp Pro
    210                 215                 220

Phe Met Lys Ala Arg Leu Glu Val Ser His Glu Asp Val Leu Pro Pro
225                 230                 235                 240

Leu Ser Glu Ser Phe Asp Leu Glu Ser Leu Met Ser Thr Pro Gln Gln
                245                 250                 255

Asn Ser Ile Glu Ala Glu Ala Asn Ser Ser Ser Phe Phe Asp Phe Gly
            260                 265                 270

Phe Pro Asp Asn Phe Thr Leu Glu Glu Phe Met Leu Asn
        275                 280                 285

<210> SEQ ID NO 33
<211> LENGTH: 285
<212> TYPE: PRT
<213> ORGANISM: Brassica campestris

<400> SEQUENCE: 33

Met Gly Arg Ser Pro Cys Cys Asp Lys Asn Gly Val Lys Lys Gly Pro
1               5                   10                  15

Trp Thr Ser Glu Glu Asp Gln Lys Leu Ile Asp Tyr Ile Arg Phe His
            20                  25                  30

Gly Pro Gly Asn Trp Arg Thr Leu Pro Lys Asn Ala Gly Leu Gln Arg
        35                  40                  45
```

```
Cys Gly Lys Ser Cys Arg Leu Arg Trp Thr Asn Tyr Leu Arg Pro Asp
    50              55                  60

Ile Lys Arg Gly Arg Phe Ser Phe Glu Glu Glu Thr Ile Ile Gln
65              70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
            100                 105                 110

Arg Lys Arg Leu Val Arg Ser Ala Ile Asp Pro Val Thr His Ser Pro
            115                 120                 125

Arg Leu Asp Leu Leu Asp Ile Ser Ser Leu Leu Ala Ala Leu Ile Asn
    130                 135                 140

Gln Pro Asn Phe Ser Ser Val Ala Thr His Ala Ser Ser Leu Leu His
145                 150                 155                 160

Pro Asp Val Leu Arg Leu Ala Ser Leu Leu Leu Pro Pro Gln Gln Pro
                165                 170                 175

Leu Gln Asn Phe Asn Pro Ile Tyr Ala Pro Asn Leu Asp Gln Asn Ile
                180                 185                 190

Gln Thr Pro Ile Thr Thr Val Ser Ser Gln Asp Ser Gln Leu Gln Ala
            195                 200                 205

Glu Cys Thr Thr Pro Val Ser Asn Asn Glu Thr Ser Ser Phe Asp Pro
    210                 215                 220

Phe Met Lys Ala Arg Leu Glu Val Ser His Glu Asp Val Leu Pro Pro
225                 230                 235                 240

Leu Ala Glu Ser Leu Asp Leu Glu Ser Leu Met Ser Thr Pro Gln Gln
                245                 250                 255

Asn Ser Ile Glu Ala Glu Ala Asn Ser Ser Ser Phe Phe Asp Phe Gly
            260                 265                 270

Leu Pro Asp Asn Phe Thr Phe Glu Asp Phe Met Leu Asn
            275                 280                 285
```

```
<210> SEQ ID NO 34
<211> LENGTH: 301
<212> TYPE: PRT
<213> ORGANISM: Dinothrombium tinctorium

<400> SEQUENCE: 34
```

```
Met Arg Val Ser Lys Lys Ser Val Val Phe Ile Phe Lys Leu Phe Phe
1               5                   10                  15

Asn Phe Pro Ala Phe Ile Ser Ser Lys Glu Cys Lys Thr Asp Asp Ser
                20                  25                  30

Gln Met Asn Gly Ser Asn Ser Glu Thr Leu Asn Ser Asn Asp Tyr Tyr
            35                  40                  45

Cys Thr Glu Ser Ile Thr Asp Ile Asp Ser Asp Leu Arg Thr Pro Ile
    50                  55                  60

Lys Asp Arg Pro Met Asp Ser Val Ala Ile Tyr Lys Asn His Asn Leu
65              70                  75                  80

Asp Asp Asn Ser Thr Ser Glu Glu Leu Glu Asn Leu Asp Pro Tyr Tyr
                85                  90                  95

Phe Ile Arg Asn Leu Pro Pro Leu Thr Lys Glu Met Ile Ala Arg Asn
                100                 105                 110

Pro Ala Leu Pro Leu Lys Thr Arg Ser Ser Pro Glu Phe Thr Leu Val
            115                 120                 125

Leu Asp Leu Asp Glu Thr Leu Val His Cys Ser Leu Thr Glu Leu Glu
    130                 135                 140
```

-continued

```
Asp Ala Thr Phe Thr Phe Pro Val Ile Phe Gln Asp Asn Glu Tyr Lys
145                 150                 155                 160

Val Phe Val Arg Thr Arg Pro Tyr Phe Lys Glu Phe Leu Glu Lys Val
                165                 170                 175

Ser Gln Leu Phe Glu Val Ile Leu Phe Thr Ala Ser Lys Lys Val Tyr
                180                 185                 190

Ala Asp Lys Leu Leu Asn Leu Leu Asp Pro Glu Arg Lys Tyr Ile Lys
            195                 200                 205

Tyr Arg Leu Phe Arg Glu His Cys Val Cys Ile Lys Gly Asn Tyr Ile
    210                 215                 220

Lys Asp Leu Asn Ile Leu Gly Arg Asp Leu Ala Lys Thr Ile Ile Ile
225                 230                 235                 240

Asp Asn Ser Pro Gln Ala Phe Gly Tyr Gln Ile Glu Asn Gly Ile Pro
                245                 250                 255

Ile Glu Ser Trp Phe Met Asp Gln Ser Asp Lys Glu Leu Val Asn Leu
                260                 265                 270

Val Pro Phe Leu Glu Ser Leu Val Ser Leu Asn Glu Asp Val Arg Pro
            275                 280                 285

His Ile Cys Asn Arg Tyr His Leu Lys Lys Tyr Ile Cys
    290                 295                 300

<210> SEQ ID NO 35
<211> LENGTH: 281
<212> TYPE: PRT
<213> ORGANISM: Brassica campestris

<400> SEQUENCE: 35

Met Gly Arg Ser Pro Cys Cys Asp Lys Asn Gly Val Lys Lys Gly Pro
1               5                   10                  15

Trp Thr Ser Glu Glu Asp Gln Lys Leu Ile Asp Tyr Ile Arg Phe His
                20                  25                  30

Gly Pro Gly Asn Trp Arg Thr Leu Pro Lys Asn Ala Gly Leu Gln Arg
            35                  40                  45

Cys Gly Lys Ser Cys Arg Leu Arg Trp Thr Asn Tyr Leu Arg Pro Asp
    50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
            100                 105                 110

Arg Lys Arg Leu Val Arg Ser Gly Ile Asp Pro Val Thr His Ser Pro
        115                 120                 125

Arg Leu Asp Leu Leu Asp Ile Ser Ser Leu Leu Ala Ala Leu Ile Asn
    130                 135                 140

Gln Pro Asn Phe Ser Ser Val Ala Thr His Ala Ser Ser Leu Leu His
145                 150                 155                 160

Pro Asp Val Leu Arg Leu Ala Ser Leu Leu Leu Pro Pro Gln Gln Pro
                165                 170                 175

Leu Gln Asn Phe Asn Pro Ile Tyr Ala Pro Asn Leu Asp Gln Asn Ile
                180                 185                 190

Gln Thr Pro Ile Thr Thr Val Ser Ser Gln Asp Ser Gln Leu Gln Ala
            195                 200                 205

Glu Cys Thr Thr Pro Val Ser Asn Asn Glu Thr Ser Ser Phe Asp Pro
```

```
        210              215              220

Phe Met Lys Ala Arg Leu Glu Leu Lys Val Lys Gly Gly Ser Lys Lys
225              230              235              240

Thr Thr Thr Asp Arg Glu Ser Lys Met Met Gly Lys Asp Cys Gln Leu
                 245              250              255

Met Gly Leu Thr Trp Leu Leu Ala Arg Asn Lys Thr Val Tyr Ile Pro
             260              265              270

Thr Val Ser Ala Lys Ser His Tyr Val
         275              280

<210> SEQ ID NO 36
<211> LENGTH: 281
<212> TYPE: PRT
<213> ORGANISM: Brassica napus

<400> SEQUENCE: 36

Met Gly Arg Ser Pro Cys Cys Asp Lys Asn Gly Val Lys Lys Gly Pro
1               5               10              15

Trp Thr Ser Glu Glu Asp Gln Lys Leu Ile Asp Tyr Ile Arg Phe His
                20              25              30

Gly Pro Gly Asn Trp Arg Ile Leu Pro Lys Asn Ala Gly Leu Gln Arg
         35              40              45

Cys Gly Lys Ser Cys Arg Leu Arg Trp Thr Asn Tyr Leu Arg Pro Asp
     50              55              60

Ile Lys Arg Gly Arg Phe Ser Phe Glu Glu Glu Glu Thr Ile Ile Gln
65              70              75              80

Leu His Ser Val Met Gly Asn Lys Trp Ser Ala Ile Ala Ala Arg Leu
                85              90              95

Pro Gly Arg Thr Asp Asn Glu Ile Lys Asn His Trp Asn Thr His Ile
             100             105             110

Arg Lys Arg Leu Val Arg Ser Gly Ile Asp Pro Val Thr His Ser Pro
         115             120             125

Arg Leu Asp Leu Leu Asp Ile Ser Ser Leu Leu Ala Ala Leu Ile Asn
         130             135             140

Gln Pro Asn Phe Ser Ser Val Ala Thr His Ala Ser Ser Leu Leu His
145             150             155             160

Pro Asp Val Leu Arg Leu Ala Ser Leu Leu Leu Pro Pro Gln Gln Pro
                 165             170             175

Leu Gln Asn Phe Asn Pro Ile Tyr Ala Pro Asn Leu Asp Gln Asn Ile
             180             185             190

Gln Thr Pro Ile Thr Thr Val Ser Ser Gln Asp Ser Gln Leu Gln Ala
         195             200             205

Glu Cys Thr Thr Pro Val Ser Asn Asn Glu Thr Ser Ser Phe Asp Pro
         210             215             220

Phe Met Lys Ala Arg Leu Glu Leu Lys Val Lys Gly Gly Ser Lys Lys
225              230              235              240

Thr Thr Thr Asp Arg Glu Ser Lys Met Met Gly Lys Asp Cys Gln Leu
                 245             250             255

Met Gly Leu Thr Trp Leu Leu Ala Arg Asn Lys Thr Val Tyr Ile Pro
             260             265             270

Thr Val Ser Ala Lys Ser His Tyr Val
         275             280

<210> SEQ ID NO 37
<211> LENGTH: 198
```

<212> TYPE: PRT
<213> ORGANISM: Arabidopsis thaliana

<400> SEQUENCE: 37

Met Asn Ile Arg Trp Ser Ala Ile Ala Ala Arg Leu Pro Gly Arg Thr
1               5                   10                  15

Asp Asn Glu Ile Lys Asn His Trp Asn Thr His Ile Arg Lys Arg Leu
                20                  25                  30

Val Arg Ser Gly Ile Asp Pro Val Thr His Ser Pro Arg Leu Asp Leu
            35                  40                  45

Leu Asp Leu Ser Ser Leu Leu Ser Ala Leu Phe Asn Gln Pro Asn Phe
        50                  55                  60

Ser Ala Val Ala Thr His Ala Ser Ser Leu Leu Asn Pro Asp Val Leu
65                  70                  75                  80

Arg Leu Ala Ser Leu Leu Leu Pro Leu Gln Asn Pro Asn Pro Val Tyr
                85                  90                  95

Pro Ser Asn Leu Asp Gln Asn Leu Gln Thr Pro Asn Thr Ser Ser Glu
            100                 105                 110

Ser Ser Gln Pro Gln Ala Glu Thr Ser Thr Val Pro Thr Asn Tyr Glu
            115                 120                 125

Thr Ser Ser Leu Glu Pro Met Asn Ala Arg Leu Asp Asp Val Gly Leu
        130                 135                 140

Ala Asp Val Leu Pro Pro Leu Ser Glu Ser Phe Asp Leu Asp Ser Leu
145                 150                 155                 160

Met Ser Thr Pro Met Ser Ser Pro Arg Gln Asn Ser Ile Glu Ala Glu
                165                 170                 175

Thr Asn Ser Ser Thr Phe Phe Asp Phe Gly Ile Pro Glu Asp Phe Ile
            180                 185                 190

Leu Asp Asp Phe Met Phe
        195

<210> SEQ ID NO 38
<211> LENGTH: 539
<212> TYPE: PRT
<213> ORGANISM: Artemisia annua

<400> SEQUENCE: 38

Met Thr Lys Ser Leu Gly Arg Asn Asp Lys Asn Lys Lys Gln Asn Asn
1               5                   10                  15

Asn Gly Asp Ile Leu Gly Leu Gly Ile Arg Val Lys Lys Gly Pro Trp
                20                  25                  30

Thr Pro Glu Glu Asp Arg Lys Leu Leu Ser Tyr Ile Gln Gln Tyr Gly
            35                  40                  45

His Gly Ser Trp Arg Ser Leu Pro Val Lys Ala Gly Leu Lys Arg Cys
        50                  55                  60

Gly Lys Ser Cys Arg Leu Arg Trp Thr Asn Tyr Leu Arg Pro Asp Ile
65                  70                  75                  80

Lys Arg Gly Lys Phe Ser Leu Glu Glu Glu Arg Lys Ile Ile Gln Leu
                85                  90                  95

His Ala Leu Leu Gly Asn Arg Trp Ser Thr Ile Ala Ala His Leu Pro
            100                 105                 110

Arg Arg Thr Asp Asn Glu Ile Lys Asn His Trp Asn Ser His Ile Lys
            115                 120                 125

Lys Arg Met Thr Lys Met Gly Ile Asp Pro Met Thr His Lys Pro Lys
        130                 135                 140

```
Ser Gly Thr Gln Leu Leu Gly Thr Asn Leu Asn His Met Ala Gln Trp
145                 150                 155                 160

Glu Ala Ala Arg Leu Glu Ala Glu Ala Arg Leu Val Gln Lys Pro Lys
                165                 170                 175

Asn His Leu Asn Gln Leu Ser Tyr Asn His Val Ser Pro Gln Ser Ile
                180                 185                 190

His Lys Thr Pro Thr Pro Leu Pro Pro Gln Asn Leu Pro Cys Leu Asp
            195                 200                 205

Val Leu Lys Met Thr Lys Ser Leu Gly Arg Asn Asp Lys Asn Lys Lys
        210                 215                 220

Gln Asn Asn Asn Gly Asp Ile Leu Gly Leu Gly Ile Arg Val Lys Lys
225                 230                 235                 240

Gly Pro Trp Thr Pro Glu Glu Asp Arg Lys Leu Leu Ser Tyr Ile Gln
                245                 250                 255

Gln Tyr Gly His Gly Ser Trp Arg Ser Leu Pro Val Lys Ala Gly Leu
                260                 265                 270

Lys Arg Cys Gly Lys Ser Cys Arg Leu Arg Trp Thr Asn Tyr Leu Arg
            275                 280                 285

Pro Asp Ile Lys Arg Gly Lys Phe Ser Leu Glu Glu Glu Arg Lys Ile
        290                 295                 300

Ile Gln Leu His Ala Leu Leu Gly Asn Arg Trp Ser Thr Ile Ala Ala
305                 310                 315                 320

His Leu Pro Arg Arg Thr Asp Asn Glu Ile Lys Asn His Trp Asn Ser
                325                 330                 335

His Ile Lys Lys Arg Met Thr Lys Met Gly Ile Asp Pro Met Thr His
            340                 345                 350

Lys Pro Lys Ser Gly Thr Gln Leu Leu Gly Thr Asn Leu Asn His Met
            355                 360                 365

Ala Gln Trp Glu Ala Ala Arg Leu Glu Ala Glu Ala Arg Leu Val Gln
        370                 375                 380

Lys Pro Lys Asn His Leu Asn Gln Leu Ser Tyr Asn His Val Ser Pro
385                 390                 395                 400

Gln Ser Ile His Lys Thr Pro Thr Pro Leu Pro Pro Gln Asn Leu Pro
                405                 410                 415

Cys Leu Asp Val Leu Lys Val Trp Gln Gly Asn Leu Trp Thr Asn Tyr
                420                 425                 430

Ser Ile Asn Asn Glu Ser Leu Gln Ser Leu Ile Ser Arg Pro Lys Val
            435                 440                 445

Ser Val Glu Thr Pro Val Met Pro Val Ser Asn Asn Val Lys Ser Asn
        450                 455                 460

Gly Thr Cys Gly Gln Gly Pro Thr Met Lys His Asn Asp Gln Ile Glu
465                 470                 475                 480

Thr Gln Met Gly Pro Phe Asp Glu Phe Glu Phe Ala Asn Asp Ala Asn
                485                 490                 495

Phe Ile Asn Asp Asp Pro Leu Arg Ser Pro Gly Phe Trp Lys Glu Leu
                500                 505                 510

Ile Asp Val Leu Asp Gly Gly Trp Asn Ser Leu Thr Ser Asn Phe Ala
            515                 520                 525

Leu Met Asp Ser Pro Pro Ala Ser Pro Val Phe
        530                 535
```

<210> SEQ ID NO 39
<211> LENGTH: 589
<212> TYPE: PRT

-continued

<213> ORGANISM: Artemisia annua

<400> SEQUENCE: 39

```
Met Thr Lys Ser Leu Gly Arg Asn Asp Glu Asn Lys Lys Gln Asn Asn
1               5                   10                  15

Asn Gly Asp Ile Leu Gly Leu Gly Ile Arg Val Lys Lys Gly Pro Trp
            20                  25                  30

Thr Pro Glu Glu Asp Arg Lys Leu Leu Ser Tyr Ile Gln Gln Tyr Gly
            35                  40                  45

His Gly Ser Trp Arg Ser Leu Pro Val Lys Ala Gly Leu Lys Arg Cys
        50                  55                  60

Gly Lys Ser Cys Arg Leu Arg Trp Thr Asn Tyr Leu Arg Pro Asp Ile
65                  70                  75                  80

Lys Arg Gly Lys Phe Ser Leu Glu Glu Glu Arg Lys Ile Ile Gln Leu
                85                  90                  95

His Ala Leu Leu Gly Asn Arg Trp Ser Thr Ile Ala Ala His Leu Pro
            100                 105                 110

Arg Arg Thr Asp Asn Glu Ile Lys Asn His Trp Asn Ser His Ile Lys
            115                 120                 125

Lys Arg Met Thr Lys Met Gly Ile Asp Pro Met Thr His Met Pro Lys
        130                 135                 140

Ser Gly Thr Gln Leu Leu Gly Thr Asn Leu Asn His Met Ala Gln Trp
145                 150                 155                 160

Glu Ala Ala Arg Leu Glu Ala Glu Ala Arg Leu Val Gln Lys Pro Lys
                165                 170                 175

Asn His Leu Asn Gln Leu Ser Tyr Asn His Val Ser Pro Gln Ser Ile
            180                 185                 190

His Lys Thr Pro Thr Pro Leu Pro Pro Gln Asn Leu Pro Cys Leu Asp
        195                 200                 205

Val Leu Lys Val Trp Gln Gly Asn Leu Trp Thr Asn Tyr Ser Ile Asn
    210                 215                 220

Asn Glu Ser Leu Gln Ser Leu Ile Ser Arg Pro Lys Val Ser Val Glu
225                 230                 235                 240

Thr Pro Val Met Pro Val Ser Asn Asn Val Lys Ser Asn Gly Thr Cys
                245                 250                 255

Gly Gln Gly Ile Lys Met Thr Lys Ser Leu Gly Arg Asn Asp Lys Asn
            260                 265                 270

Lys Lys Gln Asn Asn Asn Gly Asp Ile Leu Gly Leu Gly Ile Arg Val
        275                 280                 285

Lys Lys Gly Pro Trp Thr Pro Glu Glu Asp Arg Lys Leu Leu Ser Tyr
    290                 295                 300

Ile Gln Gln Tyr Gly His Gly Ser Trp Arg Ser Leu Pro Val Lys Ala
305                 310                 315                 320

Gly Leu Lys Arg Cys Gly Lys Ser Cys Arg Leu Arg Trp Thr Asn Tyr
                325                 330                 335

Leu Arg Pro Asp Ile Lys Arg Gly Lys Phe Ser Leu Glu Glu Glu Arg
            340                 345                 350

Lys Ile Ile Gln Leu His Ala Leu Leu Gly Asn Arg Trp Ser Thr Ile
        355                 360                 365

Ala Ala His Leu Pro Arg Arg Thr Asp Asn Glu Ile Lys Asn His Trp
    370                 375                 380

Asn Ser His Ile Lys Lys Arg Met Thr Lys Met Gly Ile Asp Pro Met
385                 390                 395                 400
```

-continued

```
Thr His Lys Pro Lys Ser Gly Thr Gln Leu Leu Gly Thr Asn Leu Asn
                405                 410                 415

His Met Ala Gln Trp Glu Ala Ala Arg Leu Glu Ala Glu Ala Arg Leu
                420                 425                 430

Val Gln Lys Pro Lys Asn His Leu Asn Gln Leu Ser Tyr Asn His Val
                435                 440                 445

Ser Pro Gln Ser Ile His Lys Thr Pro Thr Pro Leu Pro Pro Gln Asn
            450                 455                 460

Leu Pro Cys Leu Asp Val Leu Lys Val Trp Gln Gly Asn Leu Trp Thr
465                 470                 475                 480

Asn Tyr Ser Ile Asn Asn Glu Ser Leu Gln Ser Leu Ile Ser Arg Pro
                485                 490                 495

Lys Val Ser Val Glu Thr Pro Val Met Pro Val Ser Asn Asn Val Lys
                500                 505                 510

Ser Asn Gly Thr Cys Gly Gln Gly Pro Thr Met Lys His Asn Asp Gln
            515                 520                 525

Ile Glu Thr Gln Met Gly Pro Phe Asp Glu Phe Glu Phe Ala Asn Asp
            530                 535                 540

Ala Asn Phe Ile Asn Asp Asp Pro Leu Arg Ser Pro Gly Phe Trp Lys
545                 550                 555                 560

Glu Leu Ile Asp Val Leu Asp Gly Gly Trp Asn Ser Leu Thr Ser Asn
                565                 570                 575

Phe Ala Leu Met Asp Ser Pro Pro Ala Ser Pro Val Phe
                580                 585

<210> SEQ ID NO 40
<211> LENGTH: 475
<212> TYPE: PRT
<213> ORGANISM: Solanum lycopersicum

<400> SEQUENCE: 40

Met Asp Lys Leu Ile Asn Gln Glu Asn Asn Ile Asp Lys Glu Ile Met
1               5                   10                  15

Glu Leu Arg Arg Gly Pro Trp Thr Val Glu Glu Asp Leu Val Leu Met
                20                  25                  30

Asn Tyr Ile Ser His His Gly Glu Gly Arg Trp Asn Ser Leu Ser Arg
                35                  40                  45

Cys Ala Gly Leu Lys Arg Thr Gly Lys Ser Cys Arg Leu Arg Trp Leu
            50                  55                  60

Asn Tyr Leu Arg Pro Asp Val Arg His Gly Asn Ile Thr Leu Glu Glu
65                  70                  75                  80

Gln Leu Leu Ile Leu Gln Leu His Ser Arg Trp Gly Asn Arg Trp Ser
                85                  90                  95

Lys Ile Ala Gln His Leu Pro Gly Arg Thr Asp Asn Glu Ile Lys Asn
                100                 105                 110

Tyr Trp Arg Thr Arg Val Gln Lys His Ala Lys Gln Leu Lys Cys Asp
                115                 120                 125

Val Asn Ser Lys Gln Phe Gln Asp Thr Leu Gln Ile Met Glu Leu Arg
            130                 135                 140

Arg Gly Pro Trp Thr Val Glu Glu Asp Phe Ile Leu Met Asn Tyr Ile
145                 150                 155                 160

Ser His His Gly Glu Gly Arg Trp Asn Ser Leu Ser Arg Cys Ala Gly
                165                 170                 175

Leu Lys Arg Thr Gly Lys Ser Cys Arg Leu Arg Trp Leu Asn Tyr Leu
                180                 185                 190
```

-continued

```
Arg Pro Asn Ile Arg His Gly Asn Ile Thr Leu Glu Glu Gln Leu Leu
        195                 200                 205

Ile Leu Gln Leu His Phe Arg Trp Gly Asn Arg Trp Ser Lys Ile Ala
    210                 215                 220

Glu His Leu Pro Gly Arg Thr Asp Asn Glu Ile Lys Asn Tyr Trp Arg
225                 230                 235                 240

Thr Arg Val Gln Lys His Ala Lys Gln Leu Lys Cys Asp Val Asn Ser
            245                 250                 255

Lys Gln Phe Lys Asp Thr Leu Arg Tyr Leu Trp Ile Pro Arg Leu Val
            260                 265                 270

Glu Arg Ile Glu Ala Ser Lys Ile Ser Asn Asn Asn Cys Ile Asn Glu
        275                 280                 285

Ala Gln Arg Ser Val Thr Ser Thr Ser Val Thr Leu Glu Asn Ser Ser
        290                 295                 300

Val Ala Thr Ser Ser Glu Asn Ser Asn Gln Asp Tyr Asn Gln Val Asn
305                 310                 315                 320

Gln Ser Asp Glu Asn Asn Asn Asn Leu Asp Leu Lys Arg Gly Ser Trp
            325                 330                 335

Thr Val Glu Glu Asp Phe Thr Leu Met Asn His Ile Ala Leu His Gly
            340                 345                 350

Glu Gly Arg Trp Asn Ser Leu Ala Arg Ser Ala Gly Leu Lys Arg Thr
            355                 360                 365

Gly Lys Ser Cys Arg Leu Arg Trp Leu Asn Tyr Leu Arg Pro Asp Val
    370                 375                 380

Arg Arg Gly Asn Ile Thr Leu Glu Glu Gln Leu Leu Ile Leu Gln Leu
385                 390                 395                 400

His Ser Arg Trp Gly Asn Arg Trp Ser Lys Ile Ala Gln Tyr Leu Pro
            405                 410                 415

Gly Arg Thr Asp Asn Glu Ile Lys Asn Tyr Trp Arg Thr Arg Val Gln
            420                 425                 430

Lys Gln Ala Lys Gln Leu Lys Cys Asp Val Asn Ser Lys Glu Phe Lys
        435                 440                 445

Asp Thr Leu His Tyr Leu Trp Ile Pro Arg Leu Val Glu Arg Ile Gln
    450                 455                 460

Ala Ser Ser Asn Ser Asn Ser Asn Asn Gln Gly
465                 470                 475

<210> SEQ ID NO 41
<211> LENGTH: 463
<212> TYPE: PRT
<213> ORGANISM: Populus trichocarpa

<400> SEQUENCE: 41

Met Gly Arg Ser Pro Cys Cys Ser Lys Glu Gly Leu Asn Arg Gly Ala
1               5                   10                  15

Trp Thr Ala Leu Glu Asp Lys Ile Leu Met Ala Tyr Ile Lys Ala His
            20                  25                  30

Gly Glu Ser Asn Trp Arg Asn Leu Pro Glu Arg Ala Gly Leu Lys Arg
            35                  40                  45

Cys Gly Lys Ser Cys Arg Leu Arg Trp Leu Asn Tyr Leu Arg Pro Asp
    50                  55                  60

Ile Arg Arg Gly Asn Ile Ser His Asp Glu Glu Glu Leu Ile Ile Arg
65                  70                  75                  80

Leu His Asn Leu Leu Gly Asn Arg Trp Ser Val Ile Ala Gly Arg Leu
```

-continued

```
                 85              90              95
Pro Gly Arg Thr Gly Asn Glu Ile Lys Asn Tyr Trp Asn Thr Thr Leu
             100             105             110

Gly Lys Lys Ala Lys Gly Glu Ser Ser Ser Gln Ser Lys Gln Ser Cys
             115             120             125

Gln Ser Lys Ser Arg Ala Ile Lys Pro Met Thr Ser Thr Gln Pro Ser
         130             135             140

Lys Ser Thr Gln Thr Thr Gln Val Ile Arg Thr Lys Ala Thr Thr Cys
145             150             155             160

Thr Lys Cys Ala Trp Lys Glu Met Gly Arg Ser Pro Cys Cys Ser Lys
             165             170             175

Glu Gly Leu Asn Arg Gly Ala Trp Thr Ala Leu Glu Asp Lys Thr Leu
             180             185             190

Met Ala Tyr Ile Lys Ala His Gly Glu Gly Asn Trp Arg Asn Leu Pro
             195             200             205

Glu Arg Ala Gly Leu Lys Arg Cys Gly Lys Ser Cys Arg Leu Arg Trp
         210             215             220

Leu Asn Tyr Leu Arg Pro Asp Ile Lys Arg Gly Asn Ile Ser His Asp
225             230             235             240

Glu Glu Glu Leu Ile Ile Arg Leu His Asn Leu Leu Gly Asn Arg Trp
             245             250             255

Ser Val Ile Ala Gly Arg Leu Pro Gly Arg Thr Asp Asn Glu Ile Lys
             260             265             270

Asn Tyr Trp Asn Thr Thr Leu Gly Lys Lys Ala Lys Gly Glu Ser Ser
             275             280             285

Ser Gln Ser Lys Gln Ser Cys Gln Ser Lys Ser Arg Ala Ile Lys Pro
         290             295             300

Met Thr Ser Thr Gln Pro Ser Lys Ser Thr Gln Thr Thr Gln Val Ile
305             310             315             320

Arg Ile Lys Ala Thr Arg Cys Thr Lys Val Leu Leu Ser Leu Gln Ser
             325             330             335

Pro Pro Pro Thr Arg Thr Pro Leu Pro Pro Glu Ile Leu Ser Ser
             340             345             350

Thr Ala Met Asn Asp Pro Ser Gln Ala Ser Leu Ile Asn His Gln Gln
             355             360             365

Asp Gly Pro Asn Phe His Cys Gly Thr Glu Glu Val His Ala Cys His
         370             375             380

Asp Gly Ser Asp Phe Phe Asn Phe Gly Lys Trp Asn Glu Ile Gln Pro
385             390             395             400

Asn Asp Ile Asp Gly Asp Thr Leu Met Lys Ser Gly Cys Asn Arg Asn
             405             410             415

Leu Ser Arg Gly Ser Glu Cys Ser Leu Gly Ile Phe Asp Asp Leu Met
             420             425             430

Phe Lys Asp Trp Ala Leu Asn His Cys Pro Glu Asp Asn Ala Thr Leu
             435             440             445

Asp Leu Glu Ser Leu Ala His Leu Leu Asp Ser Glu Glu Trp Pro
     450             455             460
```

<210> SEQ ID NO 42
<211> LENGTH: 396
<212> TYPE: PRT
<213> ORGANISM: Malus domestica

<400> SEQUENCE: 42

-continued

```
Met Gly Pro Phe Pro Val Lys Gly Asn Thr Ser Asn Phe Trp His Lys
1               5                   10                  15

Thr Ser Thr Lys Leu His Gln Asp Leu Met Pro Cys Tyr Glu Lys Tyr
            20                  25                  30

Glu Ile Asn Lys Gly Ala Trp Ser Lys Gln Glu Asp Gln Lys Leu Ile
        35                  40                  45

Asp Tyr Ile Gln Lys His Gly Glu Gly Cys Trp Asn Ser Leu Pro His
    50                  55                  60

Ala Ala Gly Leu Ser Arg Cys Gly Lys Ser Cys Arg Leu Arg Trp Ile
65                  70                  75                  80

Asn Tyr Leu Arg Pro Asp Leu Lys Arg Glu Ser Ile Arg Glu Asp Glu
                85                  90                  95

Glu Asp Leu Ile Ile Arg Leu His Ala Leu Leu Gly Asn Arg Trp Ser
            100                 105                 110

Leu Ile Ala Gly Arg Leu Pro Gly Arg Thr Asp Asn Glu Val Lys Asn
            115                 120                 125

Tyr Trp Asn Thr His Ile Arg Lys Lys Leu Leu Lys Met Gly Ser Thr
    130                 135                 140

Leu Asp Pro Lys Lys Pro His His His Asn Asp Pro His Leu Arg Lys
145                 150                 155                 160

Gly Thr Thr Ala Thr Val Pro Leu Leu Gln Pro Asp Thr Ser Ser Pro
                165                 170                 175

Ile Ser Phe Ala Leu Ser Ser Ser Asp Ser Met Ser Thr Gly Ala Glu
            180                 185                 190

Ile His Ser Asn Lys Ser Gly Lys Pro Cys Cys Glu Lys Arg Lys Thr
            195                 200                 205

Asn Lys Gly Ala Trp Ser Lys Gln Glu Asp Glu Lys Leu Thr Gln Tyr
    210                 215                 220

Val Glu Lys Asn Gly Glu Gly Ser Trp Arg Ser Leu Pro Leu Ala Ala
225                 230                 235                 240

Gly Leu Leu Arg Cys Gly Lys Ser Cys Arg Leu Arg Trp Val Asn Tyr
                245                 250                 255

Leu Arg Pro Asn Val Lys Arg Gly Asn Phe Gly Glu Asp Glu Glu Asp
            260                 265                 270

Leu Ile Ile Arg Leu His Ala Leu Leu Gly Asn Arg Trp Ser Leu Ile
            275                 280                 285

Ala Gly Arg Leu Pro Gly Arg Thr Asp Asn Glu Val Lys Asn Tyr Trp
    290                 295                 300

Asn Thr His Leu Arg Arg Lys Leu Ile Gln Met Gly Val Asp Pro Asn
305                 310                 315                 320

Asn His Arg Ile Gly His Thr His Asn Ile Gly Leu Thr Lys Pro Ser
            325                 330                 335

Phe Gly Ser Arg Lys Val Asn Tyr Pro Ser Lys Pro Val Asn Ser Gln
            340                 345                 350

Gly Asp Lys Asp Ser Asp His Ile Lys Pro Leu Ser Asp Ser Thr Ser
            355                 360                 365

Gly Pro Glu Ser Asn Thr Ser Cys Ser Gly Leu Pro Asp Leu Asn Leu
    370                 375                 380

Asp Leu Thr Ile Gly Pro Leu Ser Ser Phe Gly Tyr
385                 390                 395
```